(12) United States Patent
Dekany et al.

(10) Patent No.: US 8,785,594 B2
(45) Date of Patent: Jul. 22, 2014

(54) GLYCOPROTEINS AND GLYCOSYLATED CELLS AND A METHOD FOR THE PREPARATION OF THE SAME

(75) Inventors: Gyula Dekany, Queensland (AU); Károly Ágoston, Telki (HU); István Bajza, Debrecen (HU); Marie Bøjstrup, Tåstrup (DK); Lars Kröger, Hamburg (DE)

(73) Assignee: Glycom A/S, Lyngby (DK)

( * ) Notice: Subject to any disclaimer, the term of this patent is extended or adjusted under 35 U.S.C. 154(b) by 155 days.

(21) Appl. No.: 12/733,672

(22) PCT Filed: Sep. 24, 2008

(86) PCT No.: PCT/EP2008/062728
§ 371 (c)(1),
(2), (4) Date: May 6, 2010

(87) PCT Pub. No.: WO2009/040363
PCT Pub. Date: Apr. 2, 2009

(65) Prior Publication Data
US 2010/0261873 A1    Oct. 14, 2010

(30) Foreign Application Priority Data
Sep. 25, 2007  (DK) .................................. 2007 01381

(51) Int. Cl.
*A61K 38/14*    (2006.01)
*C07K 9/00*    (2006.01)
(52) U.S. Cl.
USPC ........................................................ 530/322
(58) Field of Classification Search
USPC ........................................................ 530/322
See application file for complete search history.

(56) References Cited

FOREIGN PATENT DOCUMENTS

| EP | 0441192 | 8/1991 |
|---|---|---|
| WO | WO 88/27562 | 4/1988 |

OTHER PUBLICATIONS

Pearce et al., Angew. Chem. Int. Ed., 2005, 44, 1057-1061.*
Ichikawa et al, Organic Letters, 2006, 8(22), 5009-5012.*
Yoshiyasu Ichikawa, "Synthesis of Urea-Tethered Neoglycoconjugates and Pseudooligosaccharides in Water." Journal of the American Chemical Society, Mar. 29, 2006, vol. 128, No. 12, pp. 3934-3938.
Daniel Specker, et al., "Synthesis and Application of Glycopeptide and Glycoprotein Mimetics." Glycopeptides and Glycoproteins-:Synthesis, Structure, and Application. Springer-Verlag Berlin Heidelberg. Dec. 21, 2006. pp. 65-107.
Bruno Drouillat, et al. "Solid Phase Synthesis of C-Terminal Carbohydrate Modified Enkephalins." Bioorganic & Medicinal Chemistry Letters. Elsevier Science, Great Britain. vol. 7, No. 17. pp. 2247-2250, 1997.
Yoshiyasu Ichikawa, et al. "Urea Glycoside Synthesis in Water." Synlett, May 6, 2004. pp. 1019-1022, Mar. 3, 2012.
Scott Laughlin, et al. "Metabolic Labeling of Glycans with Azido Sugars for Visualization and Glycoproteomics." Methods in Enzymology—Glycobiology 2006. vol. 415. pp. 230-250.

\* cited by examiner

*Primary Examiner* — Elli Peselev
(74) *Attorney, Agent, or Firm* — McHale & Slavin, P.A.

(57) ABSTRACT

The present application discloses novel glycoproteins and a related glycosylcarbamoylation methodology suitable for the preparation of glycopeptides (in particular glycoproteins and glycosylated cells), as well as the use of such glycoproteins in medicine, e.g. as pharmaceuticals and diagnostics or in diagnostic kits. A method for the preparation of a carbohydrate-peptide conjugate includes reacting a cyclic carbamate with a peptide which has at least one primary amino group.

19 Claims, 4 Drawing Sheets

GLYCOPROTEINS AND GLYCOSYLATED CELLS AND A METHOD FOR THE PREPARATION OF THE SAME

FIELD OF THE INVENTION

The present invention provides novel glycoproteins and a related glycosylcarbamoylation methodology suitable for the preparation of glycopeptides (in particular glycoproteins and glycosylated cells), as well as the use of such glycoproteins in medicine, e.g. as pharmaceuticals and diagnostics or in diagnostic kits.

BACKGROUND OF THE INVENTION

Technologies suitable for the preparation of glycoconjugates such as glycopeptides, glycoproteins, glycolipids, glycosylated cell surfaces, glycosylated cell membranes and other glycosylated non-biological surfaces have a great importance in drug discovery and glycobiology. Such enabling technologies play essential roles in the development of glycopharmaceuticals by conjugating immunogenic and non-immunogenic carbohydrate moieties to chemical and/or biological entities. The most advanced technologies are usually based upon the use of ligation chemistries, in which protecting group assistance is avoided during the conjugation of ligating probes to target chemical and biological entities.

Several ligation methodologies have been described in scientific literature focusing on the substitution of N-terminal and lysine side-chains of peptides and proteins in order to deliver the desired carbohydrates moieties. It is well-known that primary amino functional groups are abundant in all kind of biological samples such as organs, skin, fur, silk, cell surfaces and could also be easily displayed on synthetic polymers. Thus, primary amine selective ligation methodologies have the greatest potentials to provide products of many kinds for numerous industries.

Primary amine ligation chemistries have to provide proper reactivities, chemoselectivities, often satisfactory site-selectivities in water or other aqueous solutions while eliminating the occurrence of severe by-product formation. By-product formation of primary-amine specific ligations is due to unwanted reactions at numerous nucleophilic functional groups such as secondary amino, alcoholic and phenolic hydroxyl, carboxyl, etc present in both the ligating probes and the targeted multifunctional molecules/biological entities.

Several primary amine-specific ligation methodologies have been introduced in the past. These ligation processes have severe shortcomings regarding to the achieved substitution degree and selectivities.

The above mentioned primary amine ligation techniques often suffer from low degree of substitution or low degree of chemoselectivity due to the use of very reactive ligating probes such as mixed anhydrides. In several cases, the use of activating agents is also necessary complicating work-up procedures and lowering product purities (mixed anhydride method, reductive amination).

Furthermore, in some ligation methodologies toxic or hard to remove condensation by-products could form causing serious problems in the derivatisation of sensitive biological entities (2-iminomethoxymethylthio ligation, acyl azide ligation, squaric acid ligation). In most of the cases, the developed methodologies use linker systems containing artificial and/or toxic residues (coupling with aryl-isothiocyanates, squaric acid ligation) limiting the scope of ligations by the introduction of unnecessary linking moieties.

Thus, there is a demand for the development of new ligation methodologies suitable for conjugations of carbohydrates to proteins in view of the limitations of present technologies. Novel methodologies have to fulfill the following criteria:

The ligation reaction should preferably work in aqueous solutions, preferably in water
A direct linkage between the conjugated moieties should preferably be established, thereby eliminating the use of artificial linkers.
Natural and non-toxic linker moieties can be accepted.
Coupling reagents should be avoided during the ligation reaction.
Condensation by-product formation should be eliminated.
The ligation chemistry should be capable of working in a wide pH range.
The reactivity of ligating probes should support both chemoselectivity and site-selectivity while rapid conjugations could be achieved.

EP 441192 A2 discloses retroisosteric dipeptides and their use as rennin inhibitors.

WO 88/02756 A2 discloses sugar derivatives of a biologically active peptide with prolonged duration of action.

BRIEF DESCRIPTION OF THE INVENTION

The present invention provides the desired ideal ligation procedure by linking unprotected carbohydrates directly to peptides/proteins/biological entities in water, in broad pH ranges and without the use of any coupling reagent. Furthermore, the newly developed method provides an excellent chemo- and site-selectivity.

Hence, one aspect of the present invention relates to a method for the preparation of a carbohydrate-peptide conjugate, cf. claim 1.

Another aspect of the present invention relates to carbohydrate-peptide conjugates, cf. claims 7, 8 and 10.

A third aspect of the present invention relates to such carbohydrate-peptide conjugates for use in medicine, cf. claim 15.

A fourth aspect of the present invention relates to the use of a carbohydrate-peptide conjugate as a pharmaceutical, a diagnostic agent, or in a diagnostic kit, cf. claim 17.

A fifth aspect of the present invention relates to novel cyclic carbamates of oligosaccharides.

DETAILED DESCRIPTION OF THE INVENTION

Figure 1:
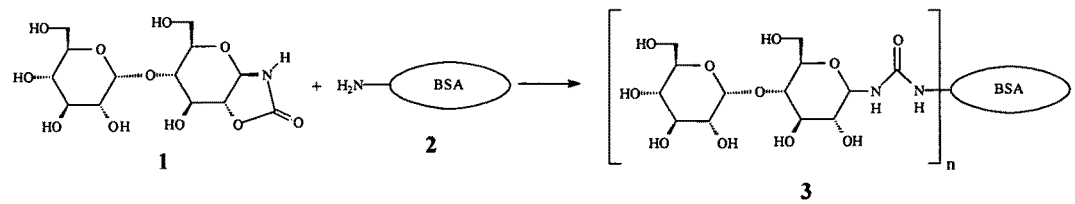
FIG. 1. Specific reaction scheme of a carbohydrate cyclic carbamate ligation using a disaccharide ligating probe.

As mentioned above, the present invention, i.a., relates to a method for the preparation of a carbohydrate-peptide conjugate, said method comprising the step of reacting a cyclic carbamate (4)

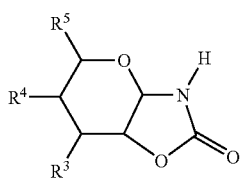
(4)

wherein $R^3$ and $R^4$ are independently selected from the group consisting of hydroxyl, acetamido, and a carbohydrate moiety; and $R^5$ is selected from the group consisting of hydrogen, methyl, hydroxymethyl, acetamidomethyl, carboxyl, and $X-(CH_2)_r-$, wherein X is a carbohydrate moiety and r is an integer selected from 0, 1, 2 and 3;
with a peptide, said peptide comprising at least one primary amino group.

Chemical modification of biological and chemical entities is one of the most important reactions which can provide products characterized by new physical, chemical, biological and physiological properties. One of the most desired structural modifications of biopolymers and biological entities is glycosylation. Glycoconjugates are natural structures providing new properties of peptides/proteins, and biological cell surfaces. For example, carbohydrate-peptide conjugates can stabilize the optimal conformation of the peptide (e.g. protein) in question thereby maintaining the desired function. Carbohydrate-peptide conjugates can also represent increased half-life, water solubility and enhanced stabilities of proteins. Covalently linked carbohydrates could also serve as immunodeterminants on the surface of viruses, pro- and eukaryotic cells. Several carbohydrate moieties are known to inhibit adhesion of microorganisms, while others act as receptors for binding of those. Thus, glycoconjugates play important roles in viral and bacterial infections and certain derivatives could be used as anti-infectives.

Hence, in the present context, the term "carbohydrate-peptide conjugate" is intended to mean a conjugate of a carbohydrate and a peptide, e.g. as outlined in the following by means of the conjugates of the General Formulae 1 and 2 (see further below). It should be understood that the conjugate comprises one or more carbohydrate moieties and a peptide moiety. Such carbohydrate moieties may in themselves be mono-, di- or oligosaccharides.

Indeed, the term "carbohydrate moiety" (also referred to as the glycosyl moiety) is—when used herein—intended to encompass (but not being limited to) derivatised and underivatised mono-, di-, oligosaccharides, N-, S- and C-glycosides. A carbohydrate moiety may represent a linear or branched (often a highly branched) structure, consisting of monosaccharide units. Some of the more abundantly used monosaccharide units include glucose, N-acetyl-glucosamine, mannose, galactose, neuraminic acid, N-acetylneuraminic acid, etc.

The term "peptide" is—when used herein—intended to encompass smaller peptides, e.g. oligopeptides having from 5 amino acid units, and up to polypeptides and proteins having from 30 amino acid units. Typically, the peptide/peptide moiety comprises a total of at least 30 amino acid units, typically α-amino acids linked together by means of amide bonds (peptide bonds). In more interesting embodiments, the total number of amino acid units is typically at least 60, such as at least 100, or even at least 150. The larger peptides/peptide moieties may even consist of two or more domains relevant for the formation of biologically peptides/proteins, e.g. enzymes, therapeutically relevant proteins, etc.

The cyclic carbamate (4) represents a key reagent for the formation of the carbohydrate-peptide conjugate.

In the cyclic carbamate, $R^3$ and $R^4$ are independently selected from the group consisting of hydroxyl, acetamido, and a carbohydrate moiety. Moreover, $R^5$ is selected from the group consisting of hydrogen, methyl, hydroxymethyl, acetamidomethyl, carboxyl, and $X-(CH_2)_r-$, wherein X is a carbohydrate moiety and r is an integer selected from 0, 1, 2 and 3.

It should be understood that in the most intriguing embodiments, the cyclic carbamate represent a di-, tri- or oligosaccharide, i.e. at least one of $R^3$, $R^4$ and X represents a carbohydrate moiety.

As examples of interesting variants of the cyclic carbamate compounds can be mentioned compounds having the cyclic carbamate moiety at the 1,2-N,O-position of the reducing end of the di- and oligosaccharides (4a), (4b), and (4c):

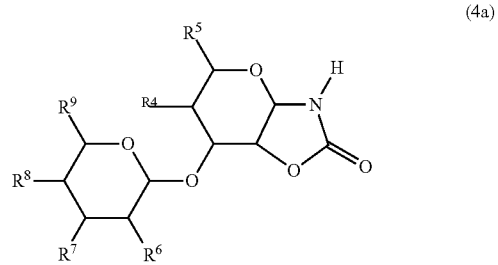
(4a)

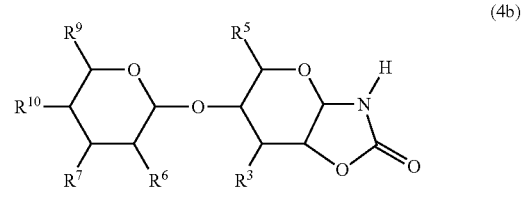
(4b)

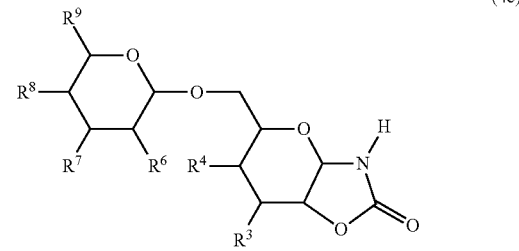
(4c)

wherein $R^6$ and $R^7$ are as defined for $R^3$ and $R^4$ above, $R^9$ is as defined for $R^5$ above, and $R^8$ and $R^{10}$ are independently selected from the group consisting of hydroxyl, $C_{1-6}$-alkoxy, $C_{2-20}$-acyloxy, acetamido, and a carbohydrate moiety.

The term "$C_{1-6}$-alkoxy" means "$C_{1-6}$-alkyl-oxy", where "$C_{1-6}$-alkyl" is intended to mean a linear or branched hydrocarbon group having 1 to 6 carbon atoms, such as methoxy, ethoxy, propyloxy, iso-propyloxy, butyloxy, pentyloxy, and hexyloxy.

The term "$C_{2-20}$-acyloxy" means "$C_{1-19}$-alkyl-C(=O)—O—", where "$C_{1-19}$-alkyl" is intended to mean a linear or branched hydrocarbon group having 1 to 19 carbon atoms, such as acetyloxy, ethylcarbonyloxy, propylcarbonyloxy, iso-propylcarbonyloxy, butylcarbonyloxy, pentylcarbonyloxy, octylcarbonyloxy, etc., as well as unsaturated variants thereof, e.g. those where "$C_{2-20}$-acyloxy" has the meanings "$C_{1-19}$-alkylene-C(=O)—O—", "$C_{1-19}$-alkyl-di-ene-C(=O)—O—", "$C_{1-19}$-alkyl-tri-ene-C(=O)—O—", "$C_{1-19}$-alkyl-tetra-ene-C(=O)—O—", "$C_{1-19}$-alkynyl-C(=O)—O—", etc., etc.

Reaction Between Cyclic Carbamate and Peptide

The peptides relevant in the present context are those having at least one primary amino group which can undergo reaction with the cyclic carbamate. It will be appreciated that some peptides include several primary amines, e.g. side chain primary amines originating from lysine amino acid units and N-terminal primary amines originating from various amino acids (excluding, however, proline).

The step of reacting the cyclic carbamate (4) with the peptide involves contacting of the species under conditions which will facilitate reaction between one or more primary amino groups and a corresponding number of cyclic carbamate molecules.

The ligation reaction can be illustrated as by the following reaction scheme where (4) represents the 1,2-N,O-cyclic carbamate ($R^3$, $R^4$ and $R^5$ defines as above) and (2) represents one primary amino group ($H_2N$) of a peptide ($E^1$), and the resulting carbohydrate-peptide conjugate is represented by (3):

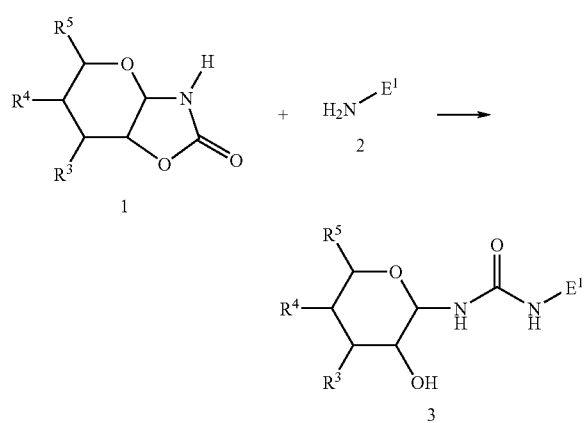

A ring-opening reaction of carbohydrate cyclic carbamates (4) with N-nucleophiles of primary amines found in peptides/proteins, biological entities, etc. (2) is the key chemistry of the novel ligating process. The ligation becomes very powerful in cases, when cyclic carbamates (4) is characterized by trans-trans fused two-ring system. Such an extremely strained ring system prefers stabilization via ring-opening processes. The preparation of cyclic carbamates such as (4) will be discussed later.

A chemoselective and site-selective novel ligation reaction of the corresponding cyclic carbamate of carbohydrates to chemical and biological entities expressing primary amino groups is typically carried out in either organic or aqueous solutions at temperatures ranges 0-40° C. in acidic, neutral or basic reaction conditions. Solvents including but not limited to methanol, water, ethanol, acetone, toluene, benzene, 1,4-dioxane, DMF, pyridine, etc and the mixtures of thereof can be used for such chemical transformations. Basic substances such as inorganic/organic bases—especially, N,N-diisopropylethylamine, triethylamine, etc—and salts of thereof might be preferred during the substitution in order to control pH, catalytic procedures and site-selectivities. Acidic substances such as inorganic/organic acids—preferably HCl, acetic acid, formic acid, etc—and salts of thereof such as $NaH_2PO_4$ could be used. The reaction time for the substitution typically varies from 3-24 hours depending on the structures of substrates, the set temperature and the cyclic carbamates of carbohydrates. A conjugated product of glycoconjugate is typically obtained in yields ranging from 80 to 95%. It is important to emphasize that site-selectivity between N-terminal and lysine side-chain substitution could easily maintained by pH adjustment and setting proper reaction conditions. Thus, ligation reactions carried out at pH 4-7 usually display excellent N-terminal selectivities. Conjugations at higher pH 8-10 provide predominantly lysine side-chain modified products. The novel ligation works in water at pH 7 without the addition of any base/acid or any other activating agent. Furthermore, the resulted products have natural glycosylurea linkages, which cannot be considered to be toxic or harmful for living systems.

Hence, in one embodiment of the method according to the present invention, the reaction takes place in a polar solvent, such as water.

In some embodiments of the method according to the present invention, the reaction takes place at a pH of in the range of 6.5-10.5. Alternatively, the reaction takes place at a pH in the range of 4.0-7.0 in order to facilitate selective ligation at the N-terminal, or at a pH in the range of 8.0-10.0 in order to facilitate selective ligation at lysine side chains.

The method is applicable for any type of peptide, e.g. single chained peptides, multiple-chain peptides, folded peptides, aggregated peptides, cell-surface bound proteins, cell-membrane bound proteins, etc.

In one particularly interesting embodiment, the peptide is a cell-surface or cell-membrane bound protein.

The method gives rise to a plethora of novel carbohydrate-peptide conjugates, preferably including those defined and described further below (see "Novel carbohydrate-peptide conjugates").

Novel Carbohydrate-Peptide Conjugates

One class of novel carbohydrate-peptide conjugates are those defined by General Formula 1, in which one or more a carbohydrate moiety is linked via its glycosidic position to the ε-amino functions of lysine residues of peptides/proteins via a carbonyl linker.

Hence, the invention also relates to a carbohydrate-peptide conjugate comprising one or more moieties of the General Formula 1:

General Formula 1

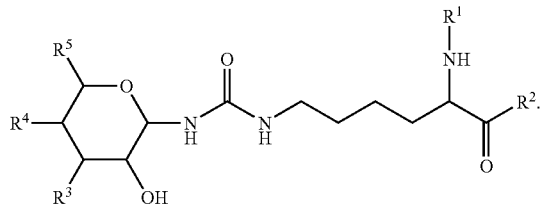

wherein
$R^1$ and $R^2$ together with the intervening lysine moiety represent a peptide moiety;
$R^3$ and $R^4$ are independently selected from the group consisting of hydroxyl, acetamido, and a carbohydrate moiety;
$R^5$ is selected from the group consisting of hydrogen, methyl, hydroxymethyl, acetamidomethyl, carboxyl, and X—$(CH_2)_r$—, wherein X is a carbohydrate moiety and r is an integer selected from 0, 1, 2 and 3;
and pharmaceutically acceptable salts thereof.

Examples hereof are carbohydrate-peptide conjugates comprising one or more moieties of any of the General Formulae 1a, 1b and 1c, General Formula 1a

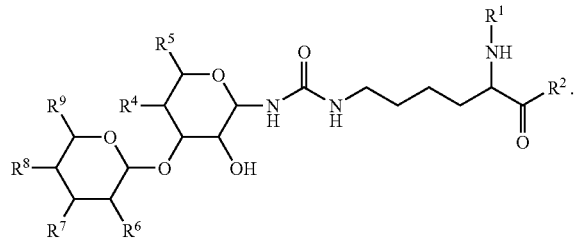

General Formula 1b

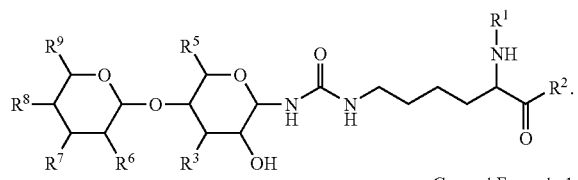

General Formula 1c

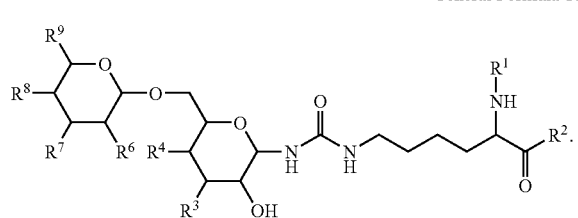

wherein $R^6$ and $R^7$ are as defined for $R^3$ and $R^4$ above, and $R^9$ is as defined for $R^5$ above, and $R^8$ is selected from the group consisting of hydroxyl, $C_{1-6}$-alkoxy, $C_{2-20}$-acyloxy, acetamido, and a carbohydrate moiety.

Another class of novel carbohydrate-peptide conjugates are those defined by General Formula 2, in which a carbohydrate moiety is linked via its glycosidic position to the N-terminal amino function of peptides/proteins via a carbonyl linker. Hence, the invention also relates to a carbohydrate-peptide conjugate comprising one or mere moieties of the General Formula 2:

General Formula 2

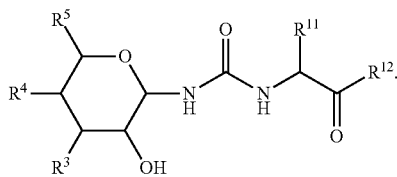

wherein
$R^{11}$ is an amino acid side chain; $R^{12}$ together with —NH—$CHR^{11}$—C=O)— represents it peptide moiety having a total number of amino acid units of at least 30; $R^3$ and $R^4$ are independently selected from the group consisting of hydroxyl, acetamido, and a carbohydrate moiety; $R^5$ is selected from the group consisting of hydrogen, methyl, hydroxymethyl, acetamidomethyl, carboxyl, and X—$(CH_2)_r$—, wherein X is a carbohydrate moiety and r is an integer selected from 0, 1, 2 and 3; and pharmaceutically acceptable salts thereof.

Examples hereof are carbohydrate-peptide conjugates comprising one or more moieties of any of the General Formulae 2a, 2b and 2c, General Formula 2a

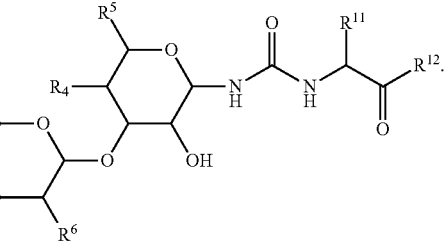

General Formula 2b

General Formula 2c

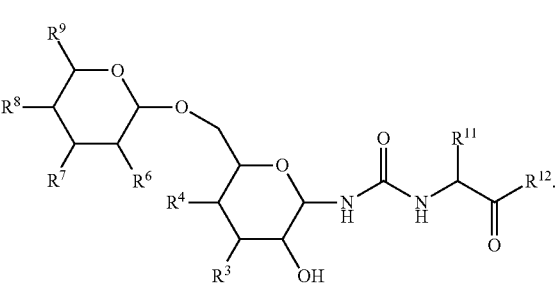

wherein $R^6$ and $R^7$ are as defined for $R^3$ and $R^4$ above, $R^9$ is as defined for $R^5$ above, and $R^8$ is selected from the group consisting of hydroxyl, $C_{1-6}$-alkoxy, $C_{2-20}$-acyloxy, acetamide, and is carbohydrate moiety.

It should be understood that the above classes of carbohydrate-peptide conjugates represented by General Formula 1 and General Formula 2 are partly overlapping in that it can readily be envisaged that one or more carbohydrate moieties are linked via their glycosidic position to the ε-amino functions of lysine residues of the peptides via a carbonyl linker and that—within the same peptide—a carbohydrate moiety is linked via its glycosidic position to the N-terminal amino function of peptides via a carbonyl linker. The peptide may—if consisting of two or more chains—even have two or more N-terminal linked carbohydrate moieties.

In some intriguing embodiments, the peptide is a cell-surface or cell-membrane bound protein.

The term "amino acid side chain" is intended to refer to the side chain group of amino acids typically included in peptides (including synthetic peptides) and is not restricted to the around 20 essential amino acids. Examples of amino acid side chains are hydrogen (representing glycine), methyl (alanine), 2-propyl (valine), 2-methyl-1-propyl (leucine), 2-butyl (isoleucine), methylthioethyl (methionine), benzyl (phenylalanine), 3-indolylmethyl (tryptophan), hydroxymethyl (serine), 1-hydroxyethyl (threonine), mercaptomethyl (cysteine), 4-hydroxybenzyl (tyrosine), aminocarbonylmethyl (asparagine), 2-aminocarbonylethyl (glutamine), carboxymethyl (aspartic acid), 2-carboxyethyl (glutamic acid), 4-amino-1-butyl (lysine), 3-guanidino-1-propyl (arginine), and 4-imidazolylmethyl (histidine).

The term "pharmaceutically acceptable salts" is intended to include acid addition salts and basic salts. Illustrative examples of acid addition salts are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids. Examples of basic salts are salts where the (remaining) counter on is selected from alkali metals, such as sodium and potassium, alkaline earth metals, such as calcium, and ammonium ions ($^+N(R)_3R'$, where R and R' independently designates optionally substituted $C_{1-6}$-alkyl, optionally substituted $C_{2-20}$-alkenyl, optionally substituted aryl, or optionally substituted heteroaryl). Pharmaceutically acceptable salts are, e.g., those described in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology. Thus, the term "an acid addition salt or a basic salt thereof" used herein is intended to comprise such salts. Furthermore, the compounds as well as any intermediates or starting materials may also be present in hydrate form.

Moreover, it should be understood that the compounds may be present as racemic mixtures or the individual stereoisomers such as enantiomers or diastereomers. The present invention encompasses each and every of such possible stereoisomers (e.g. enantiomers and diastereomers) as well as racemates and mixtures enriched with respect to one of the possible stereoisomers.

Preparation of Cyclic Carbamates

The preparation of cyclic carbamate derivatives (4) (and (4a), (4b) and (4c)) and is based on the treatment of the corresponding glycosyl azide or the corresponding other azido-deoxy-oligosaccharide derivative with carbon dioxide in the presence of trialkyl/aryl phosphines. Typically the reaction is carried out in anhydrous organic solutions at temperatures ranges 0-40° C. in neutral reaction conditions. Solvents including but not limited to acetone, toluene, benzene, 1,4-dioxane, DMF, tetrahydrofurane, etc and the mixtures of thereof can be used for such chemical transformation. The reaction time for the cyclic carbamate formation typically varies from 3-24 hours depending on the structures of substrates, the set temperature and the nature of trialkyl/arylphosphines used. The cyclic carbamate products are typically obtained in high yields of 80 to 95%.

Alternatively, the preparation of cyclic carbamate derivatives (4) (and (4a), (4b) and (4c)) is based on the treatment of the corresponding glycosyl azide or the corresponding other azido-deoxy-oligosaccharide derivative with trialkyl/aryl phosphines involved in the isolation of phosphinimine derivatives. In a second step, the phosphinimine derivatives are reacted with carbon dioxide providing the desired cyclic carbamates of oligosaccharides. Typically the reaction is carried out in anhydrous organic solutions at temperatures ranges 0-40° C. in neutral reaction conditions. Solvents including but not limited to acetone, toluene, benzene, 1,4-dioxane, DMF, tetrahydrofurane, etc and the mixtures of thereof can be used for such chemical transformation. The reaction time for the phosphinimine formation is 3-10 hours depending on the nature of trialkyl/arylphosphines used. The cyclic carbamate formation typically varies from 3-24 hours depending on the structures of substrates, the set temperature. The cyclic carbamate products are typically obtained in high yields of 80 to 95%.

Alternatively, the preparation of cyclic carbamate derivatives (4) (and (4a), (4b) and (4c)) involves the treatment of the corresponding glycosyl amine or other amino-deoxy-oligosaccharide with phosgene or other suitable phosgene derivatives such as diphosgene or triphosgene. Typically the reaction is carried out in organic or aqueous solutions at temperatures ranges 0-40° C. in neutral or basic reaction conditions. Solvents including but not limited to water, acetone, toluene, benzene, 1,4-dioxane, DMF, tetrahydrofurane, pyridine, etc and the mixtures of thereof can be used for such chemical transformation. The cyclic carbamate formation typically varies from 3-24 hours depending on the structures of substrates and the set temperature. The cyclic carbamate products are typically obtained in high yields of 80 to 95%.

Alternatively, the preparation of cyclic carbamate derivatives (4) (and (4a), (4b) and (4c)) is based on the treatment of the corresponding acyclic carbamate derivative with base such as sodium hydride or DBU initiating an intramolecular ring-dosing procedure. Typically the reaction is carried out in anhydrous organic solutions at temperatures ranges 0-40° C. in basic reaction conditions. Solvents including but not limited to toluene, benzene, 1,4-dioxane, DMF, tetrahydrofurane, etc and the mixtures of thereof can be used for such chemical transformation. The cyclic carbamate formation typically varies from 3-24 hours depending on the structures of substrates and the set temperature. The cyclic carbamate products are typically obtained in high yields of 80 to 95%.

It is important to emphasize that the cyclic carbamate derivatives (4) (and (4a), (4b) and (4c)) show excellent stabilities in several reaction conditions allowing extensive chemical derivatisation such as O-acylation, O-alkylation, cyclic acetal, cyclic ketal formation, hydrogenolysis of the unprotected derivatives. Such a unique option expands the utilities of cyclic carbamate ligating probes and could be used to ligate numerous derivatisation entities to peptides/proteins, biological and complex chemical entities.

It is believed that the cyclic carbamates of oligosaccharides (4a), (4b) and (4c), i.e.

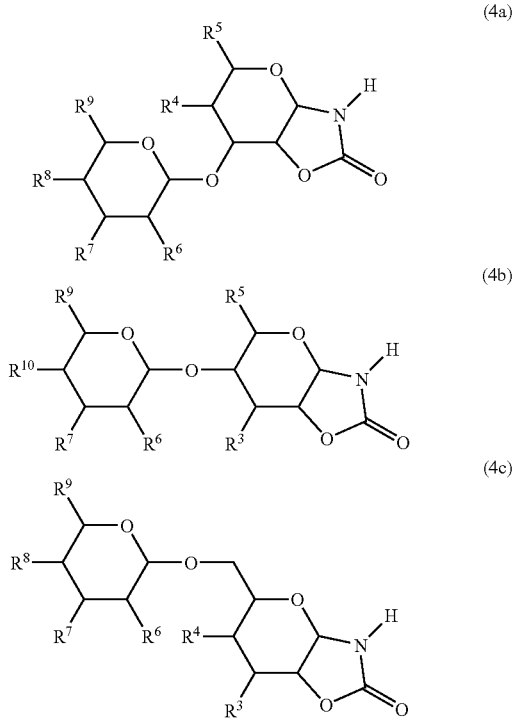

(4a)

(4b)

(4c)

wherein $R^6$ and $R^7$ are as defined for $R^3$ and $R^4$ above, and $R^9$ is as defined for $R^5$ above. $R^8$ and $R^{10}$ are independently selected from the group consisting of hydroxyl, $C_{1-6}$-alkoxy, $C_{1-6}$-acyloxy, acetamido, and a carbohydrate moiety, are novel as such, and therefore the present invention also relates to such entities, which are useful, i.a. as intermediates in the preparation of the compounds of General Formulae 2a, 2b, 2c, 3a, 3b, and 3c.

Uses of the Carbohydrate-Peptide Conjugates

Generally, the use of a carbohydrate-peptide conjugate as defined herein as a pharmaceutical, a diagnostic agent, or in a diagnostic kit.

In particular, the carbohydrate-peptide conjugates defined and described herein including those prepared according to the method defined and described herein are believed to be offer a plethora of possibilities within medicine.

In one variant, the glycosyl moiety/moieties (the carbohydrate moiety) of the carbohydrate-peptide conjugate represent(s) a non-immunogenic carbohydrate.

In one preferred embodiment several non-immunogenic carbohydrates such as dextranes, maltodextrines, maltose, cellobiose per-O-methylated oligosaccharides, thio-linked oligosaccharides could be conjugated to therapeutic peptide/protein in order to increase the half-life of those and providing beneficial physical, biological and physiological properties such as increased solubility, thermal and enzymatic stability, etc.

In another variant, the glycosyl moiety (the carbohydrate moiety) of the carbohydrate-peptide conjugate represents an immunogenic carbohydrate.

Within this variant, several immunogenic carbohydrates like ABO blood antigens, Lewis type antigens, tumor specific antigens, α-Gal-epitopes, alpha-mannosyl-epitopes, polysialyc acid can be conjugated to:

Peptides/proteins in order to down-regulate the specific peptide/protein by active vaccination.

Viruses (living, inactivated or virus particles) like HIV, Hepatitis B, Herpes, Flu, Bird flu, etc. in order to prepare vaccines against the infections.

Bacteria like *Mycobacterium, Heliobacter*, etc. in order to prepare antibacterial vaccines.

Tumor cells in order to modify immunological properties, and to generate a strong immune response via autologous cancer vaccination.

Cancer cell membranes in order to prepare autologous tumor vaccines.

In a further embodiment lipophilic oligosaccharides could be used to increase the stability of the peptide/protein by adhesion to albumin.

EXAMPLES

Part 1

Ligation

Example 1

Maltosyl cyclic carbamate 1 (40 mg) and BSA (bovine serum albumin, 50 mg) 2 were dissolved in water (5 mL) (see FIG. 1). The pH was adjusted to pH≅9.44 by the addition of triethylamine and acetic acid. The mixture was kept for 4 h at room temperature, and then the reaction mixture was transferred into a dialysis membrane and dialyzed against distillated water, for 2 days, then lyophilized obtaining 3 as a white powder.

Mass spectrometry: MALDI-TOF: Glycosylated BSA 68333, BSA ref: 66134.

Example 2

Maltosyl cyclic carbamate 1 (40 mg) and BSA (bovine serum albumin, 50 mg) 2 were dissolved in water (5 mL) (see FIG. 1). The pH was adjusted to pH≅8.57 by the addition of triethylamine and acetic acid. The mixture was kept for 4 h at room temperature, and then the reaction mixture was transferred into a dialysis membrane and dialyzed against distillated water, for 2 days, then lyophilized obtaining 3 as a white powder.

Mass spectrometry: MALDI-TOF: Glycosylated BSA 69099, BSA ref: 66134.

Example 3

Maltosyl cyclic carbamate 1 (40 mg) and BSA (bovine serum albumin, 50 mg) 2 were dissolved in water (5 mL) (see FIG. 1). The pH was adjusted to pH≅8.10 by the addition of triethylamine and acetic acid. The mixture was kept for 4 h at room temperature. The reaction mixture was transferred into a dialysis membrane and dialyzed against distillated water, for 2 days, then lyophilized obtaining 3 as a white powder.

Mass spectrometry: MALDI-TOF: Glycosylated BSA 68329, BSA ref: 66134.

Example 4

Maltosyl cyclic carbamate 1 (40 mg) and BSA (bovine serum albumin, 50 mg) 2 were dissolved in water (5 mL) (see FIG. 1). The pH was adjusted to pH≅7.45 by the addition of triethylamine and acetic acid. The mixture was kept for 4 h at room temperature. The reaction mixture was transferred into a dialysis membrane and dialyzed against distillated water, for 2 days, then lyophilized obtaining 3 as a white powder.

Mass spectrometry: MALDI-TOF: Glycosylated BSA 67679, BSA ref: 66134.

Example 5

Figure 2:
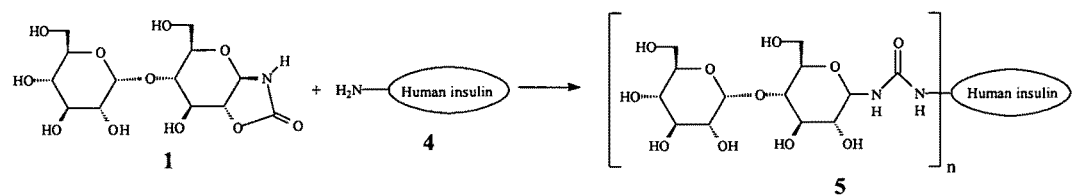
FIG. 2. Specific reaction scheme of a carbohydrate cyclic carbamate ligation using a disaccharide ligating probe for the glycosylation of Human Insulin.

Maltosyl cyclic carbamate 1 (10 mg) and human insulin 4 (50 mg) were dissolved in water (13 mL) (see FIG. 2). The pH was adjusted to pH≅10.00 by the addition of diisopropylethylamine and aqueous $NaH_2PO_4$. The mixture was kept for 2.5 h at room temperature then the reaction mixture was lyophilized providing B29 glycosylated insulin 5 in more than 90% site-selectivity.

Mass spectrometry: MALDI-TOF: B-29-Glycosylated Human Insulin: 6171, Human insulin: 5805.

Example 6

Maltosyl cyclic carbamate 1 (10 mg) and human insulin 4 (50 mg) were dissolved in water (13 mL) (see FIG. 2). The pH was adjusted to pH≅8.00 by the addition of diisopropyl-ethylamine and aq. $NaH_2PO_4$. The mixture was kept for 2.5 h at room temperature then the reaction mixture was lyophilized affording the modified insulin (5).

Mass spectrometry: MALDI-TOF: Glycosylated Human Insulin: 6171, Human insulin: 5804.

Example 7

Maltosyl cyclic carbamate 1 (10 mg) and human insulin 4 (50 mg) were dissolved in water (13 mL) (see FIG. 2). The pH was adjusted to pH≅7.00 by the addition of diisopropyl-ethylamine and aq $NaH_2PO_4$. The mixture was kept for 2.5 h at room temperature then the reaction mixture was lyophilized providing B-1 Glycosylated Human Insulin 5 in more than 90% site-selectivity.

Mass spectrometry: MALDI-TOF: B-1 Glycosylated Human Insulin 6171, Human insulin: 5804.

Figure 3:
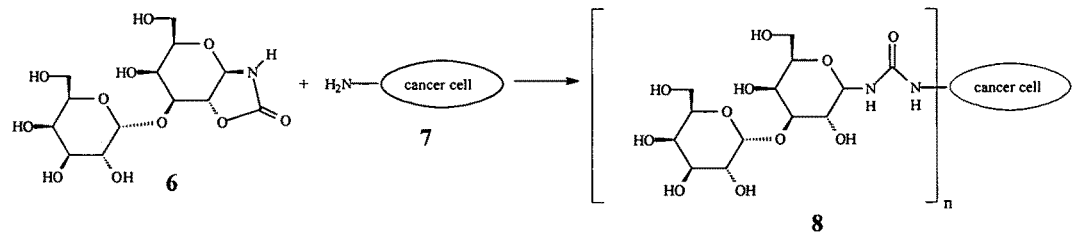
FIG. 3. Specific reaction scheme of a carbohydrate cyclic carbamate ligation using a disaccharide ligating probe to tumor cells.

Example 8

α-Gal epitope-cyclic carbamate 6 (disaccharide) (25 mg) and human breast cancer-cell line 7 ($2\times10^6$ number cell) were mixed in PBS buffer (5 mL) (see FIG. 3). The mixture was kept for 3 h at 37° C., and then the mixture was subjected to centrifugation to separate the cells from the medium.

The modified cells were treated with fluorescent labeled-lectin and the modification has been proven by flow-cytometry.

Example 9

α-Gal epitope-carbamate 6 (disaccharide) (25 mg) and human breast cancer-cell line 7 ($1\times10^6$ number cell) were mixed in PBS buffer (5 mL) (see FIG. 3). The mixture was kept for 3 h at 37° C., and then the mixture was subjected to centrifugation to separate the cells from the medium.

The modified cells were treated with fluorescent labeled-lectin and the modification has been proven by flow-cytometry.

Example 10

α-Gal epitope-carbamate 6 (disaccharide) (25 mg) and human breast cancer-cell line 7 ($5\times10^5$ number cell) were mixed in PBS buffer (5 mL) (see FIG. 3). The mixture was kept for 3 h at 37° C., and then the mixture was subjected to centrifugation to separate the cells from the medium.

The modified cells were treated with fluorescent labeled-lectin and the modification has been proven by flow-cytometry.

Figure 4:
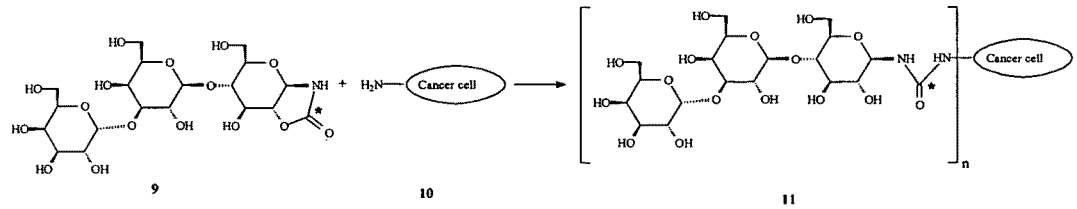
FIG. 4. General conjugation of trisaccharide to cancer cells.

From Example 11 to Example 15 Compound 9 referred as "trisaccharide probe". Reference is made to FIG. 4. The marked carbon atom labeled with C13 isotope in Example 14 and 15.

Example 11

Conjugation of Trisaccharide Probe to B16BL6 Cell Line

Cell Preparation

Two flasks (300 cm$^2$) (TPP, Trasadingen Switzerland) of confluent B16.BL6 melanoma cells grown in DMEM containing 10% fetal calf serum (without P/S) at 37.5° C. in 5% $CO_2$ were used for this experiment. Growth medium was removed from the cells and 25 mL of PBS (without $Mg^{2+}$ and $Ca^{2+}$) (Gibco Invitrogen, Taastrup, Denmark) was added to the cells and immediately removed again. Another 10 mL of PBS was added and removed, before cells were harvested with Cell Dissociation Solution C5914 (Sigma-aldrich, Saint Louis, Mo.) (3 mL per flask) and transferred to 10 mL tubes (TPP, Trasadingen Switzerland). The cells were centrifuged for 5 minutes at 300 G at 20° C. and the supernatant was discarded. Subsequently, cells were washed in PBS (without $Mg^{2+}$ and $Ca^{2+}$), centrifuged as above and resuspended in PBS (without $Mg^{2+}$ and $Ca^{2+}$). The concentration of the cell suspension was determined.

Conjugation of Alpha-Gal Epitopes to B16.BL6 Melanoma Cells

Five hundred mg of alpha-Gal trisaccharide-carbamate (9) was dissolved in PBS (without $Mg^{2+}$ and $Ca^{2+}$) (Gibco Invitrogen, Taastrup, Denmark) and passed through a sterile filter (Sartorius Minisart®, 0.20 my) (Sartorius, Goettingen, Germany). Eight different concentrations of conjugate were prepared. Two mL of each conjugate dilution was added to a flask with 2 mL of PBS (without $Mg^{2+}$ and $Ca^{2+}$) and 600 µl of cell suspension containing $10^6$ B16.BL6 cells. The final volume of the flasks was 4.6 mL. The flasks were numbered 1 to 10. Flasks 1 and 10 contained no conjugate and served as controls. The cells were incubated with the conjugate for 3 hours and 25 minutes at 37° C. and 5% $CO_2$.

After conjugation, cells from conjugation reaction 1 (non-conjugated cells), 2, 4, 6 and 8 were harvested with 10 mL of Cell Dissociation Solution C5914 (Sigma-Aldrich, Saint Louis, Mo.) and transferred to 10 mL tubes (TPP, Trasadingen Switzerland). Cells were centrifuged for 5 minutes at 300 G at 20° C. and resuspended in PBS (without $Mg^{2+}$ and $Ca^{2+}$). Finally, cells were centrifuged as before and resuspended in 100 µl TBS with 1% BSA. Cell concentration and viability was determined by microscopic evaluation of trypan blue stained cell samples. Cells from conjugation reaction 3, 5, 7, 9 and 10 (non-conjugated cells), were harvested the following day as described above. The cells were centrifuged once for 5 minutes at 300 G at 20° C. and resuspended in 100 μl TBS with 1% BSA. Cell concentration and viability was determined by microscopic evaluation of trypan blue stained cell samples.

Staining of Cell Smears with FITC-Labelled GS1B4

Smears of cells from conjugation reaction 1 (non-conjugated control cells), 2, 4, 6 and 8 were incubated for 1 hour at room temperature with FITC-labelled GS1B4 diluted 1:200 in TBS. After a rinse in TBS, one drop of Fluorescent Mounting Medium (DAKO) was placed on each of the cell specimens and glass coverslips were placed on top. Binding of FITC-labelled GS1B4 to Galα1,3Gal on conjugated cells was assessed by fluorescence microscopy.

Flow Cytometry Analysis

B16.BL6 cells from conjugation reaction 1 (non-conjugated cells), 2, 4, 6 and 8 were analysed by flow cytometry. One hundred μL of cell suspension containing $1 \times 10^5$ cells were incubated for 15 minutes at 4° C. with 10 μg per mL (1:100 dilution) of FITC-labelled GS1B4 in TBS containing 1% BSA. The proportion of cells stained, mean and median cell fluorescence intensity was determined by flow cytometry. Afterwards, cells were washed once in PBS and measurements were repeated. Rabbit red blood cells (RRBC) known to express ~$2 \times 10^6$ Galα1,3Gal epitopes per cell were used for comparison. The analyses of conjugated B16.BL6 cells and RRBCs were performed on different days.

Cell Concentration and Viability after Conjugation

At the end of the conjugation procedure, both cell number and viability, assessed by trypan blue staining, were significantly reduced for all conjugation reactions. However, considerable variation between the different conjugation reactions was observed. A volume of 100 μl to 130 μl of cell suspension was obtained from each conjugation reaction.

TABLE 1

Cell concentration and viability after conjugation

| Reaction | Conjugate | Cell concentration | Cell viability |
|---|---|---|---|
| 1 | None | $2.50 \times 10^6$ cells/mL | 24.8% |
| 2 | 200 mg | $3.50 \times 10^6$ cells/mL | 58.9% |
| 3* | 100 mg | $3.08 \times 10^6$ cells/mL | 65.6% |
| 4 | 50 mg | $3.16 \times 10^6$ cells/mL | 1.9% |
| 5* | 20 mg | $1.90 \times 10^6$ cells/mL | 0.0% |
| 6 | 10 mg | $2.26 \times 10^6$ cells/mL | 16.8% |
| 7* | 5 mg | $2.02 \times 10^6$ cells/mL | 34.7% |
| 8 | 2 mg | $2.22 \times 10^6$ cells/mL | 8.1% |
| 9* | 1 mg | $2.12 \times 10^6$ cells/mL | 16.0% |
| 10* | None | $2.34 \times 10^6$ cells/mL | 20.5% |

*Cell concentration and viability measured 1 day after the conjugation procedure.

TABLE 2

Cell viability after conjugation

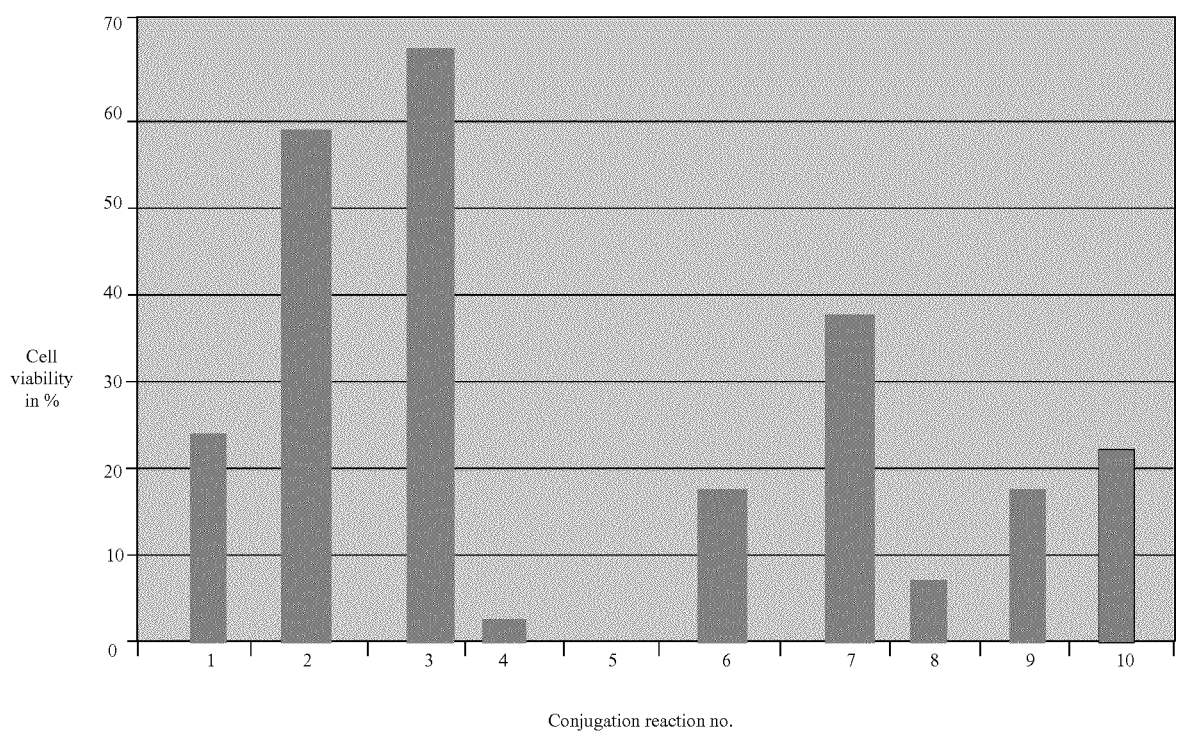

Staining of Cell Smears with FITC-Labelled GS1B4

Galα1,3Gal epitopes, detected by binding of FITC-labelled GS1B4, were found on cells from all conjugation reactions tested (conjugation reactions 2, 4, 6 and 8). None of the non-conjugated cells (conjugation reaction 1) were stained.

Figure 11:
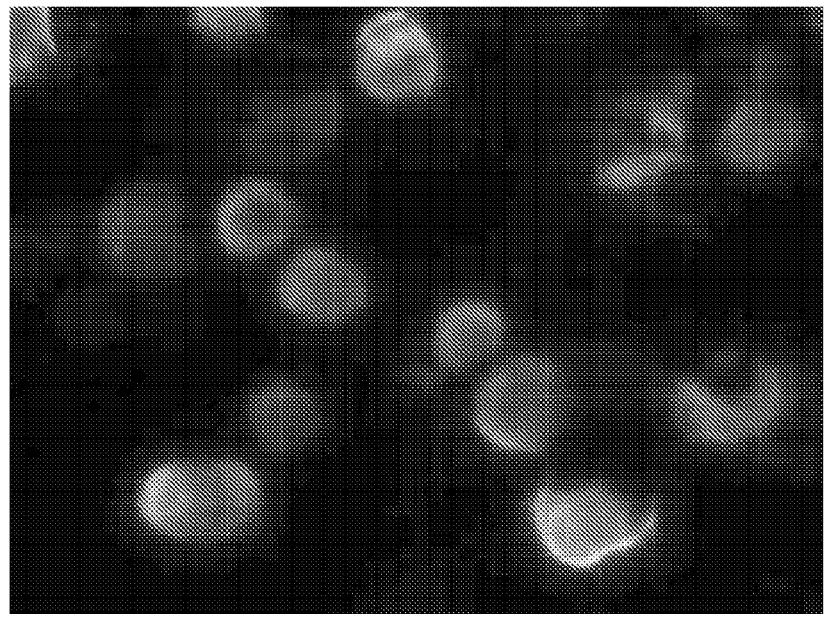
FIGS. 11 and 12. Staining of cell smears with FITC-labelled GS1B4.
Figure 12:
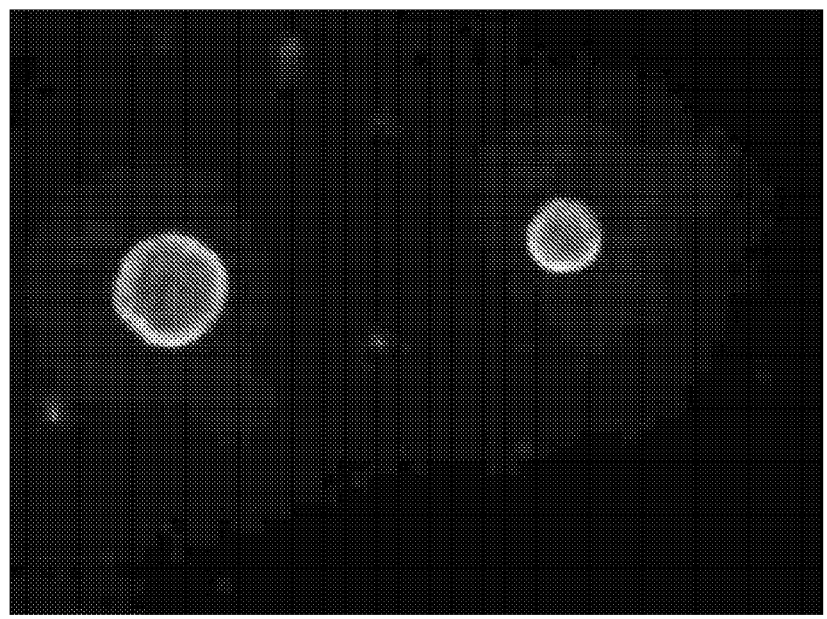

Reference is made to FIGS. 11 and 12.

Flow Cytometry

Galα1,3Gal epitopes, detected by binding of FITC-labelled GS1B4, were found on B16.BL6 cells from all conjugation reactions tested (conjugation reactions 2, 6 and 8). None of the non-conjugated control cells (conjugation reaction 1) were stained. The proportion of cells with detectable amounts of Galα1,3Gal-epitopes was determined for each of the conjugation reactions.

TABLE 3

Cells with detectable amounts of Galα1,3Gal-epitopes

| Conjugation reaction | Cells marked with FITC-GS1B4 |
|---|---|
| 0 (RRBC*) | 94.23% |
| 1 (non-conjugated cells) | 0.00% |
| 2 | 95.82% |
| 6 | 62.17% |
| 8 | 56.82% |

Fluorescence intensity of cells with detectable quantities of Galα1,3Gal-epitopes on their surfaces was measured. The results strongly indicate, that the number of Galα1,3Gal-epitopes on the conjugated cells was considerably higher than the ~2×10$^6$ Galα1,3Gal epitopes known to be present on rabbit red blood cells. Mean and median values of cell fluorescence intensity for washed and unwashed cells are shown below.

TABLE 4

Fluorescence intensity, unwashed cells

| Conjugation reaction | Mean fluorescence intensity | Median fluorescence intensity |
|---|---|---|
| 0 (RRBC*) | 38.17 | 36.52 |
| 1 (non-conjugated cells) | 8.19 | 8.43 |
| 2 | 726.72 | 523.30 |
| 6 | 862.24 | 798.63 |
| 8 | 594.99 | 572.55 |

*Rabbit red blood cells are known to express ~2 × 10$^6$ Galα1,3Gal epitopes per cell.

Visualisation of Galα1,3Gal epitopes on conjugated B16.BL6 melanoma cells from conjugation reaction 2. The cell membranes are heavily stained with FITC-labelled GS1B4 bound to Galα1,3Gal epitopes on the cell surfaces.

TABLE 5

Fluorescence intensity, washed cells

| Conjugation reaction | Mean fluorescence intensity | Median fluorescence intensity |
|---|---|---|
| 1 (non-conjugated cells) | 14.9 | 3.68 |
| 2 | 447.48 | 321.97 |
| 6 | 439.04 | 406.79 |
| 8 | 264.30 | 259.45 |

TABLE 6

Fluorescence intensity, unwashed cells

Fluorescence intensity per cell

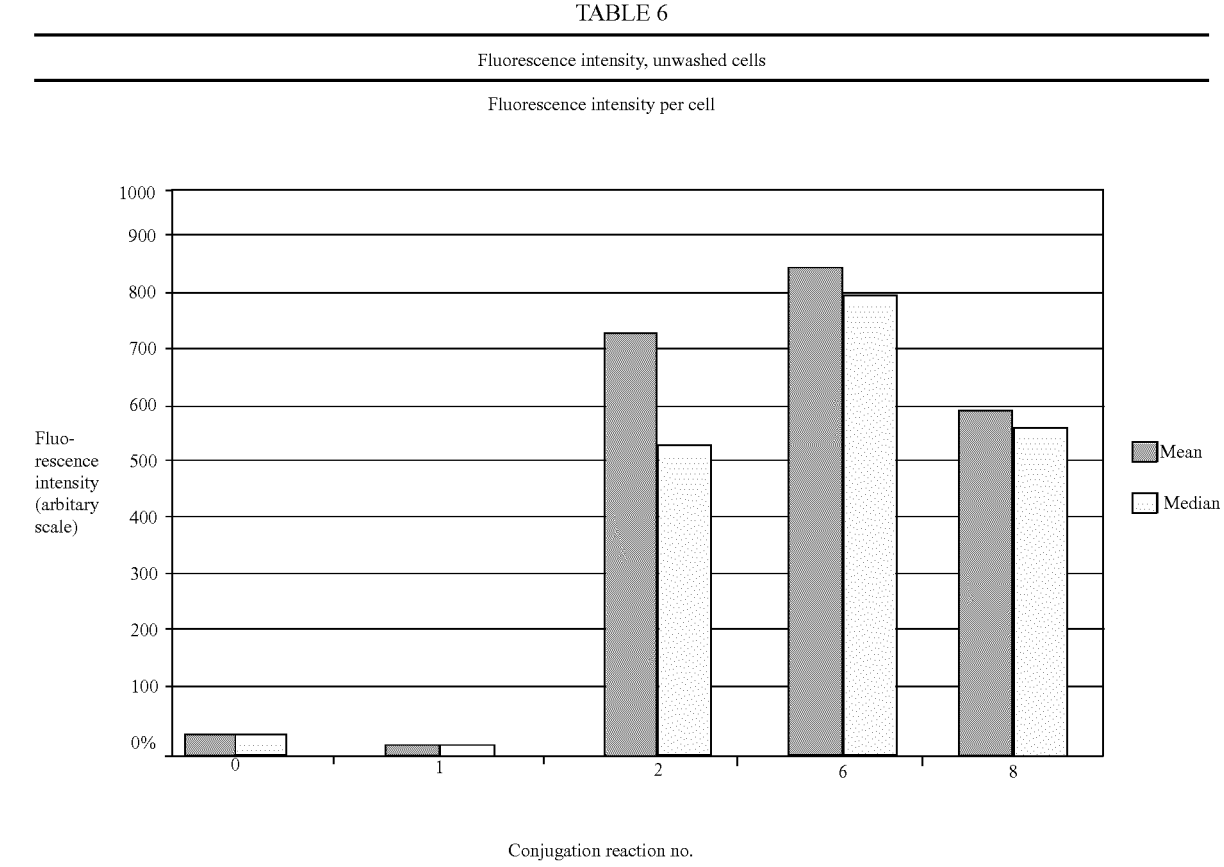

Example 12

Conjugation of Alpha-Gal Trisaccharide-Carbamate Probe to B16BL6 Cell Line

Reduction of the Conjugation Time:
Cell Preparation
  See Example 11.
Conjugation of Alpha-Gal Epitopes to B16.BL6 Melanoma Cells The alpha-Gal trisaccharide-carbamate probe (9) was dissolved in both PBS (without $Mg^{2+}$ and $Ca^{2+}$) (Gibco Invitrogen, Taastrup, Denmark) and HBSS (with D-glucose) (Gibco Invitrogen, Taastrup, Denmark) and passed through sterile filters (Sartorius Minisart®, 0.20 my) (Sartorius, Goettingen, Germany). Three different concentrations of the trisaccharide probe were prepared in both PBS and HBSS.

Eight small flasks (25 $cm^2$) (TPP, Trasadingen Switzerland) were prepared, each containing $10^6$ B16.BL6 cells, and the trisaccharide probe was added. Total volume of the flasks was 4.6 mL. The cells were incubated with the conjugate for 1 hour at 37° C. and 5% $CO_2$.

TABLE 7

| | Conjugation reactions | | |
|---|---|---|---|
| Conjugation reaction | alpha-Gal trisaccharide-carbamate (9) added | Incubation buffer | Incubation time |
| P0 | Control (no conjugate) | PBS | 1 hour |
| PA | 16 mg | PBS | 1 hour |
| PB | 2 mg | PBS | 1 hour |
| PC | 1 mg | PBS | 1 hour |
| H0 | Control (no conjugate) | HBSS (with D-glucose) | 1 hour |
| HA | 16 mg | HBSS (with D-glucose) | 1 hour |
| HB | 2 mg | HBSS (with D-glucose) | 1 hour |
| HC | 1 mg | HBSS (with D-glucose) | 1 hour |

After conjugation, the supernatant from each flask was transferred to separate 10 mL tubes (TPP, Trasadingen Switzerland). The cells were harvested with Cell Dissociation Solution (2 mL per flask) (Sigma-aldrich, Saint Louis, Mo.) and transferred to the 10 mL tubes. Cells were centrifuged for 5 minutes at 300 G at 20° C. and resuspended in 0.5 mL of PBS or HBSS. Cell concentration and viability was determined by microscopic evaluation of trypan blue stained cell samples.

After the 1-hour incubation with the trisaccharide probe most of the cells were viable and attached to the bottom surface of the flasks. However, it was very difficult to harvest these cells and most of them were lost during the procedure.

TABLE 8

| Cell viability | |
|---|---|
| Conjugation reaction | Viability of cells harvested |
| P0 | 34.6% |
| PA | 14.3% |
| PB | 32.0% |
| PC | 37.5% |
| H0 | 27.8% |
| HA | 33.3% |
| HB | 41.7% |
| HC | 41.6% |

TABLE 9

Cell viability

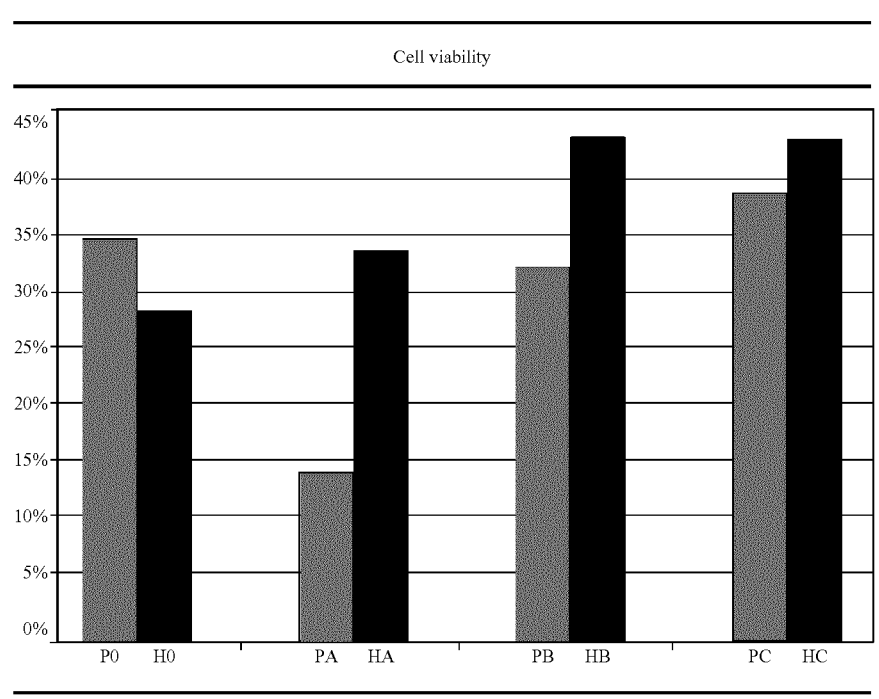

Example 13

Conjugation of Alpha-Gal Trisaccharide-Carbamate Probe (9) to B16BL6 Cell Line Reduction of the Conjugation Time:
Cell Preparation
  See Example 11.
Conjugation of Alpha-Gal Epitopes to B16.BL6 Melanoma Cells The alpha-Gal trisaccharide probe (9) was dissolved in HBSS (Gibco Invitrogen, Taastrup, Denmark) and passed through a sterile filter (0.2 μm Supor® Acrodisc® 13, Gelman Sciences, Ann Arbor, Mich.). Three different concentrations of the alpha-Gal trisaccharide-carbamate (9) were made. Five small flasks were prepared with 606 μL of cell suspension containing a total of $10^6$ B16.BL6 cells in addition to 4 mL of one of the conjugate solutions. Each flask contained a total volume of 4.6 mL. The cells were incubated with the "Glycom conjugate" for either 3 or 1.5 hours at 37° C.

TABLE 10

Conjugation reactions

| Conjugation reaction | "Glycom conjugate" | Incubation time |
|---|---|---|
| 1 | 19.2 mg | 3 hours |
| 2 | 19.2 mg | 1.5 hours |
| 3 | 1.9 mg | 1.5 hours |
| 4 | 58 mg | 1.5 hours |
| 5 | Control (no conjugate) | 1.5 hours |

After conjugation, the supernatant from each flask was transferred to separate 10 mL tubes (TPP, Trasadingen Switzerland). Cells were washed twice by adding PBS to the flasks and immediately removing it again. The cells were harvested with Cell Dissociation Solution (2 mL per flask) (Sigma-aldrich, Saint Louis, Mo.). After 5 minutes, cells were transferred to the 10 mL test tubes. The cells were centrifuged for 5 minutes at 300 G at 20° C. and resuspended in 0.5 mL of PBS. Cell concentration and viability was determined by microscopic evaluation of trypan blue stained cell samples.
Flow Cytometry Analysis
Cells from Conjugation Reaction 1:

One hundred μL of cell suspension containing $1 \times 10^5$ cells were incubated for 15 minutes at 4° C. with 10 μg per mL (1:100 dilution) of FITC-labelled GS1B4 in PBS. Rabbit red blood cells (A) were used for comparison,
Cells from Conjugation Reaction 2, 3, 4 and 5:

As very few cells were available for flow cytometry analysis the exact cell concentration was not determined. Instead, the amount of cells used was estimated to $0.4 \times 10^5$. The cells were incubated for 15 minutes at 4° C. with 4 μg per mL of FITC-labelled GS1B4 in PBS. Rabbit red blood cells (B) were used for comparison.

Mean and median cell fluorescence intensity was determined by flow cytometry.
Flow Cytometry Analysis Galα1,3Gal epitopes, detected by binding of FITC-labelled GS1B4, were found on B16.BL6 cells from all conjugation reactions. The analysis of cells from conjugation reaction 2 and 4 showed two populations of cells with different cell fluorescence intensities. The relatively high background staining indicated by the fluorescence intensity values for the non-conjugated cells (conjugation reaction 5) could be a result of a large excess amount of FITC-labelled GS1B4 added due to overestimation of the number of cells used.

TABLE 11

Fluorescence intensity, cells from conjugation reaction 1

| Conjugation reaction | Mean fluorescence intensity | Median fluorescence intensity |
|---|---|---|
| RRBC (A)* | 30.3 | 29.1 |
| 1 | 197.8 | 155.4 |

*Rabbit red blood cells are known to express ~2 × $10^6$ Galα1,3Gal epitopes per cell. 13

TABLE 12

Fluorescence intensity, cells from conjugation reaction 2, 3, 4 and 5

| Conjugation reaction | Mean fluorescence intensity | Median fluorescence intensity |
|---|---|---|
| RRBC (B)* | 25.9 | 23.7 |
| 2 (62.7% of the cells)** | 161.63 | 125.2 |
| 2 (35.3% of the cells)** | 2940.2 | 2196.8 |
| 3 | 167.8 | 66.4 |
| 4 (84.26% of the cells) | 49.2 | 44.1 |
| 4 (15.65% of the cells) | 770.0 | 504.8 |
| 5 (non-conjugated cells) | 39.56 | 32.2 |

*Rabbit red blood cells are known to express ~2 × $10^6$ Galα1,3Gal epitopes per cell.
**Two groups of cells with different fluorescence intensities were observed from both conjugation reaction 2 and 4, and therefore, values are given for both groups.

Example 14

Conjugation of the Radioactive Probe to B16BL6 Cell Line

The purpose of this experiment was to estimate the number of Galα1,3Gal epitopes conjugated to B16.BL6 melanoma cells and to compare results obtained by scintillation and flow cytometry.
Cell Preparation Nine flasks (300 cm²) (TPP, Trasadingen Switzerland) of confluent B16.BL6 melanoma cells grown in DMEM containing 10% fetal calf serum (without P/S) at 37.5° C. in 5% $CO_2$ were used for this experiment. Growth medium was removed from the cells and 20 mL of HBSS containing D-glucose (without $Mg^{2+}$ and $Ca^{2+}$) (Gibco, Invitrogen, Taastrup, Denmark) was added to the cells and immediately removed again. Another 10 mL of HBSS containing D-glucose (without $Mg^{2+}$ and $Ca^{2+}$) was added and removed, before cells were harvested with Cell Dissociation Solution C5914 (Sigma-aldrich, Saint Louis, Mo.) (10 mL per flask) and transferred to 50 mL tubes (TPP, Trasadingen Switzerland). The cells were centrifuged for 3 minutes at 300 G at 20° C. and the supernatant was discarded. Subsequently, cells were washed twice in HBSS containing D-glucose (without $Mg^{2+}$ and $Ca^{2+}$), centrifuged as above and resuspended in HBSS containing D-glucose (without $Mg^{2+}$ and $Ca^{2+}$). The concentration of the cell suspension was determined.
Conjugation of Galα1,3Gal Epitopes to B16.BL6 Melanoma Cells Radioactive labelled and regular trisaccharide probe was dissolved in HBSS containing D-glucose (without $Mg^{2+}$ and $Ca^{2+}$) (Gibco Invitrogen, Taastrup, Denmark) and passed through sterile filters (0.2 μm Supor® Acrodisc® 13, Gelman Sciences, Ann Arbor, Mich.). Four different concentrations of each "Glycom conjugate" (25 mg, 5 mg, 1 mg and 0.1 mg) were made. Twelve flasks (150 cm²) (TPP, Trasadingen Switzerland) were prepared each containing a total of $10 \times 10^6$ B16.BL6 cells. The trisaccharide probe was added and the total volume was adjusted to 20 mL with HBSS containing D-glucose (without $Mg^{2+}$ and $Ca^{2+}$). The cells were incubated with the "Glycom conjugate" for 1.5 hours at 37° C. After conjugation, the supernatant from each flask was transferred to separate 50 mL tubes (TPP, Trasadingen Switzerland). The cells were harvested with Cell Dissociation Solution C5914 (5 mL per flask) (Sigma-Aldrich, Saint Louis, Mo. and transferred to the 50 mL tubes containing the supernatant. The cells were centrifuged for 3 minutes at 300 G at 20° C. and resuspended in 5 mL of PBS (without $Mg^{2+}$ and $Ca^{2+}$). This was repeated 3 times before cell concentration and viability was determined by microscopical evaluation of trypan blue stained cell samples.

Scintillation

Cells conjugated with radioactive labelled trisaccharide probe were centrifuged for 5 minutes at 1000 G at 20° C. The supernatants were discharged and the remaining pellets were dried. Subsequently, the pellets were dissolved in 400 µl Mili-Q $H_2O$ and 1.5 mL of scintillation fluid was added. Standards for the scintillation were made by adding 500 pCi, 0.5 pCi and 0 pCi to the 3 samples of control cells. The samples were stored at room temperature for 3 days, before the cell suspensions were transferred to scintillation vials and counted.

Flow Cytometry Analysis

Cells conjugated with regular trisaccharide probe were analysed by flow cytometry. Four hundred µl of each cell suspension containing $2 \times 10^5$ cells were incubated for 15 minutes at 4° C. with 10 µg per mL of FITC-labelled GS1B4. Mean fluorescence intensity of cells stained with GS1B4 was measured by flow cytometry.

Cell Concentration and Viability after Conjugation

During the harvesting procedure, two different fractions of cells with radioactive labelled trisaccharide probe were accidentally combined and therefore had to be discharged. Consequently, the results obtained from these conjugation reactions are not comparable with the remaining. Additionally, an abnormal volume was acquired for the suspension containing cells conjugated with 0.1 mg radioactive labelled trisaccharide probe. As observed in the previous preliminary experiments, the amount of cells harvested and cell viability varied both between cells incubated with different concentrations of conjugate, and between cells incubated with regular conjugate and radioactive labeled conjugate.

TABLE 13

Cells conjugated with regular conjugate

| Conjugate added | Cell concentration* | Viability* | Cells harvested* |
|---|---|---|---|
| 0 mg (control) | $5.0 \times 10^5$ | 76.0% | $2.5 \times 10^6$ (25%) |
| 25 mg | $9.0 \times 10^5$ | 77.8% | $4.5 \times 10^6$ (45%) |
| 5 mg | $7.0 \times 10^5$ | 91.4% | $3.5 \times 10^6$ (35%) |
| 1 mg | $13.4 \times 10^5$ | 79.1% | $6.7 \times 10^6$ (67%) |
| 0.1 mg | $7.4 \times 10^5$ | 67.6% | $3.7 \times 10^6$ (37%) |

*Estimated after alpha-gal conjugation

TABLE 14

Cells conjugated with radioactive labelled conjugate

| Conjugate added | Cell concentration* | Viability* | Cells harvested* |
|---|---|---|---|
| 0 mg (control 1) | $13.8 \times 10^5$ | 87.0% | $6.9 \times 10^6$ (69%) |
| 0 mg (control 2) | $12.6 \times 10^5$ | 90.5% | $6.3 \times 10^6$ (63%) |
| 0 mg (control 3) | $11.4 \times 10^5$ | 87.8% | $5.7 \times 10^6$ (57%) |
| 25 mg** | $2.0 \times 10^5$ | 90.0% | $1.0 \times 10^6$ (10%) |
| 5 mg*** | $10.8 \times 10^5$ | 81.5% | $5.4 \times 10^6$ (54%) |
| 1 mg | $14.8 \times 10^5$ | 93.2% | $7.4 \times 10^6$ (74%) |
| 0.1 mg | $13.8 \times 10^5$ | 91.3% | $6.9 \times 10^6$ (69%) |

*Estimated after alpha-gal conjugation
**Attached cells only
***Cells from supernatant only Flow Cytometry As observed in the previous preliminary experiment, only a fraction of the conjugated cells bound detectable amounts of FITC-labelled GS1B4. The mean fluorescence intensity of cells conjugated with 1 mg was unexpectedly low, whereas a positive correlation was observed between dose of conjugate and mean fluorescence intensity for the remaining conjugation reactions.

TABLE 15

Mean fluorescence intensity

| Conjugate added | Cells marked with GS1B4 | Mean fluorescence intensity* |
|---|---|---|
| 0 mg (control) |  | 77.99 |
| 25 mg | 31.86% | 2460.67 |
| 5 mg | 14.56% | 1719.58 |
| 1 mg | 2.36% | 342.05 |
| 0.1 mg | 17.64% | 1025.86 |

*Mean Fluorescence intensity of cells marked with GS1B4

Scintillation

A positive correlation was found between the scintillation counts and dose of conjugate. However, due to the above mentioned errors made during the harvesting procedure, the results were not comparable with the results obtained from the flow cytometry analysis, and therefore an association between the two quantification methods could not be established.

TABLE 16

Estimation of epitopes per cell

| Conjugate added | Epitopes per cell |
|---|---|
| 25 mg* | $364.2 \times 10^6$ |
| 5 mg** | $152.4 \times 10^6$ |
| 1 mg | $28.3 \times 10^6$ |
| 0.1 mg | $3.6 \times 10^6$ |

*Attached cells only
**Cells from supernatant only

TABLE 17

Epitopes per cell as a function of conjugate dose

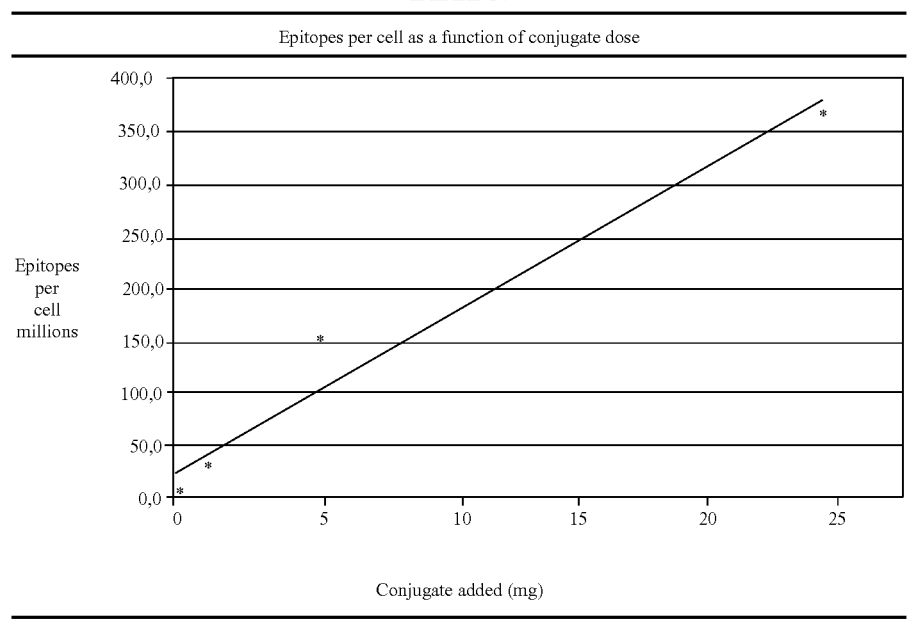

Conjugate added (mg)

Example 15

Conjugation of the Radioactive Probe to B16BL6 Cell Line

The purpose of this experiment was to estimate the number of Galα1,3Gal epitopes conjugated to B16.BL6 melanoma cells and to compare results obtained by scintillation and flow cytometry.

Cell Preparation

Twelve flasks (300 cm$^2$) (TPP, Trasadingen Switzerland) of confluent B16.BL6 melanoma cells grown in DMEM containing 10% fetal calf serum (without P/S) at 37.5° C. in 5% $CO_2$ was used for this experiment. Growth medium was removed from the cells and 20 mL of HBSS containing D-glucose (without $Mg^{2+}$ and $Ca^{2+}$) (Gibco, Invitrogen, Taastrup, Denmark) was added to the cells and immediately removed again. Another 10 mL of HBSS containing D-glucose (without $Mg^{2+}$ and $Ca^{2+}$) was added and removed, before cells were harvested with Cell Dissociation Solution C5914 (Sigma-aldrich, Saint Louis, Mo.) (10 mL per flask) and transferred to 50 mL tubes (TPP, Trasadingen Switzerland). The cells were centrifuged for 3 minutes at 300 G at 20° C. and the supernatant was discarded. Subsequently, cells were washed twice in HBSS containing D-glucose (without $Mg^{2+}$ and $Ca^{2+}$), centrifuged as above and resuspended in HBSS containing D-glucose (without $Mg^{2+}$ and $Ca^{2+}$). The concentration of the cell suspension was determined.

Conjugation of Alpha-Gal Epitopes to B16.BL6 Melanoma Cells

Radioactive labelled and regular alpha-Gal trisaccharide-carbamate (9) probe (labeled on the cyclic carbamate carbon) was dissolved in HBSS containing D-glucose (without $Mg^{2+}$ and $Ca^{2+}$) (Gibco Invitrogen, Taastrup, Denmark) and passed through sterile filters (0.2 μm Supor® Acrodisc® 13, Gelman Sciences, Ann Arbor, Mich.). Eight different concentrations of radioactive labelled alpha-Gal trisaccharide-carbamate (9) (1 μg, 10 μg, 100 μg, 1 mg, 5 mg, 10 mg, 15 mg and 20 mg) and 6 different concentrations of regular "Glycom conjugate" (10 μg, 100 μg, 1 mg, 5 mg, 10 mg, 15 mg and 20 mg) were used.

Twelve flasks (300 cm$^2$) (TPP, Trasadingen Switzerland) were prepared, each containing 10×10$^6$ B16.BL6 cells, for conjugation with the radioactive labelled trisaccharide probe, and 8 flasks (150 cm$^2$) (TPP, Trasadingen Switzerland) were prepared, each containing 5×10$^6$ B16.BL6 cells, for conjugation with the non-radioactive conjugate. The Glycom conjugate was added and the total volume was adjusted with HBSS containing D-glucose (without $Mg^{2+}$ and $Ca^{2+}$) so that each large flask (300 cm$^2$) contained a final volume of 20 mL and each medium flask (150 cm$^2$) contained a final volume of 10 mL. Cells were incubated with the "Glycom conjugate" for 1.5 hours at 37° C. After conjugation, the supernatant from each flask was transferred to separate 50 mL tubes (TPP, Trasadingen Switzerland). The cells were harvested with Cell Dissociation Solution (10 mL per large flask and 5 mL per medium flask) (Sigma-aldrich, Saint Louis, Mo.) and transferred to the 50 mL tubes containing the supernatant. The cells were centrifuged for 5 minutes at 300 G at 20° C. and resuspended in 5 mL of PBS (without $Mg^{2+}$ and $Ca^{2+}$). This was repeated 3 times before cell concentration and viability was determined by microscopic evaluation of trypan blue stained cell samples.

Scintillation

Cells incubated with radioactive labelled trisaccharide probe were centrifuged for 5 minutes at 1000 G at 20° C. The supernatant was discharged and the remaining pellets were dried. Subsequently, the pellets were dissolved in 450 μl Mili-Q $H_2O$ and 1.5 mL of scintillation fluid was added. Standards for the scintillation were made by adding 500 pCi, 0.5 pCi and 0 pCi to the 3 samples of control cells. The samples were stored at room temperature for 3 days, before the cell suspensions were transferred to scintillation vials and counted.

Flow Cytometry Analysis

Cells conjugated with regular trisaccharide probe were analysed by flow cytometry. Four hundred μl of each cell suspension containing 2×10$^5$ cells were incubated for 15 minutes at 4° C. with 10 μg per mL of FITC-labelled GS1B4. Mean fluorescence intensity of cells stained with GS1B4 was measured by flow cytometry.

TABLE 18

Cells conjugated with regular conjugate

| Conjugation reaction | Conjugate added | Cell concentration* | Viability* | Cells harvested* |
|---|---|---|---|---|
| 1 | Control | $3.4 \times 10^5$ (cells/mL) | 94.1.0% | $0.85 \times 10^6$ (17%) |
| 2 | 20 mg | $4.2 \times 10^5$ (cells/mL) | 85.7% | $1.1 \times 10^6$ (21%) |
| 3 | 15 mg | $6.0 \times 10^5$ (cells/mL) | 80.0% | $1.5 \times 10^6$ (30%) |
| 4 | 10 mg | $2.8 \times 10^5$ (cells/mL) | 71.4% | $0.7 \times 10^6$ (14%) |
| 5 | 5 mg | $4.4 \times 10^5$ (cells/mL) | 81.8% | $1.1 \times 10^6$ (22%) |
| 6 | 1 mg | $4.2 \times 10^5$ (cells/mL) | 66.7% | $1.1 \times 10^6$ (21%) |
| 7 | 100 μg | $6.0 \times 10^5$ (cells/mL) | 60.1% | $1.5 \times 10^6$ (30%) |
| 8 | 10 μg | $4.2 \times 10^5$ (cells/mL) | 57.1% | $1.1 \times 10^6$ (21%) |

*Determined after alpha-gal conjugation and after washing the cells once

TABLE 19

Cells conjugated with radioactive labelled conjugate

| Conjugation reaction | Conjugate added | Cell concentration* | Viability* | Cells harvested* |
|---|---|---|---|---|
| A | Control 1 | $5.4 \times 10^6$ (cells/mL) | 83.3% | $2.4 \times 10^6$ (24.3%) |
| B | Control 2 | $5.7 \times 10^6$ (cells/mL) | 86.3% | $2.6 \times 10^6$ (25.7%) |
| C | 20 mg | $6.1 \times 10^6$ (cells/mL) | 82.0% | $2.7 \times 10^6$ (27.5%) |
| D | 15 mg | $4.3 \times 10^6$ (cells/mL) | 88.9% | $1.9 \times 10^6$ (19.4%) |
| E | 10 mg | $12 \times 10^6$ (cells/mL) | 86.7% | $5.4 \times 10^6$ (54.0%) |
| F | 5 mg | $5.2 \times 10^6$ (cells/mL) | 82.7% | $2.3 \times 10^6$ (23.4%) |
| G | 1 mg | $5.9 \times 10^6$ (cells/mL) | 91.5% | $2.7 \times 10^6$ (26.6%) |
| H | 100 μg | $3.8 \times 10^6$ (cells/mL) | 81.6% | $1.7 \times 10^6$ (17.1%) |
| I | 10 μg | $6.2 \times 10^6$ (cells/mL) | 82.3% | $2.8 \times 10^6$ (27.9%) |
| J | 1 μg | $5.0 \times 10^6$ (cells/mL) | 84.0% | $2.3 \times 10^6$ (22.5%) |
| K | Control 3 | $5.9 \times 10^6$ (cells/mL) | 69.5% | $2.7 \times 10^6$ (26.6%) |
| L | Control 4 | $4.6 \times 10^6$ (cells/mL) | 56.5% | $2.1 \times 10^6$ (20.7%) |

*Determined after alpha-gal conjugation and after washing the cells 4 times

Flow Cytometry

Unexpectedly, no binding above background levels of FITC-labelled GS1B4 to cells from any of the conjugation reaction was detected. An additional amount of FITC-labelled GS1B4 was added to the cells and the measurements were repeated. However, again no staining was found, and, therefore, successful alpha-gal conjugation could not be confirmed by the flow cytometry analysis.

Scintillation

Due to doubts on the counting of cells conjugated with 1 mg of radioactive labeled conjugate, the results obtained for these cells are omitted. For the remaining conjugation reactions, a positive correlation was found between the scintillation counts and dose of conjugate. Due to the above mentioned lack of confirmation of successful alpha-gal conjugation by flow cytometry, an association between the two quantification methods could not be established.

TABLE 20

Cells conjugated with radioactive labelled conjugate

| Conjugate added | Cells used for scintillation | Epitopes per cell |
|---|---|---|
| 20 mg | $2.4 \times 10^6$ | $515.2 \times 10^6$ |
| 15 mg | $1.7 \times 10^6$ | $501.2 \times 10^6$ |
| 5 mg | $2.3 \times 10^6$ | $175.3 \times 10^6$ |
| 1 mg | $2.6 \times 10^6$ | $33.9 \times 10^6$ |
| 100 μg | $1.7 \times 10^6$ | $6.8 \times 10^6$ |
| 10 μg | $2.7 \times 10^6$ | $0.6 \times 10^6$ |
| 1 μg | $2.2 \times 10^6$ | $1.0 \times 10^6$ |

* Determined after alpha-gal conjugation and after washing the cells 4 times

TABLE 21

Epitopes per cell as a function of conjugate dose

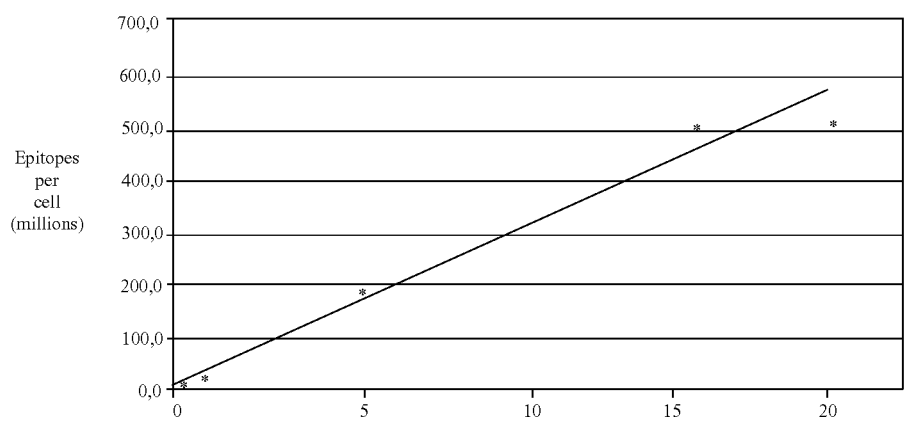

Part 2

Preparation of the Cyclic Carbamate Containing Carbohydrates

Example 16

Figure 5:
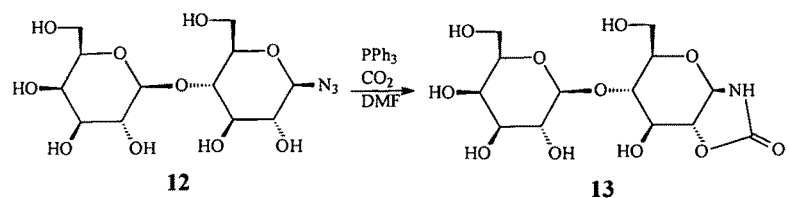
FIG. 5. Preparation of carbohydrate cyclic carbamate of lactose.

Lactosyl-azide 12 (1.5 g) was dissolved in dry DMF (40 mL) saturated with $CO_2$, then triphenyl phosphine (1.1 eq.) was added in dry DMF (5 mL) to the mixture over the period of 20 min (see FIG. 5). $CO_2$ was bubbled through the mixture for 5 h, and the mixture was stirred for 8 h. The white precipitate that formed filtered and washed with cold acetone affording the desired product 13 (1 g).

Example 17

Figure 6:
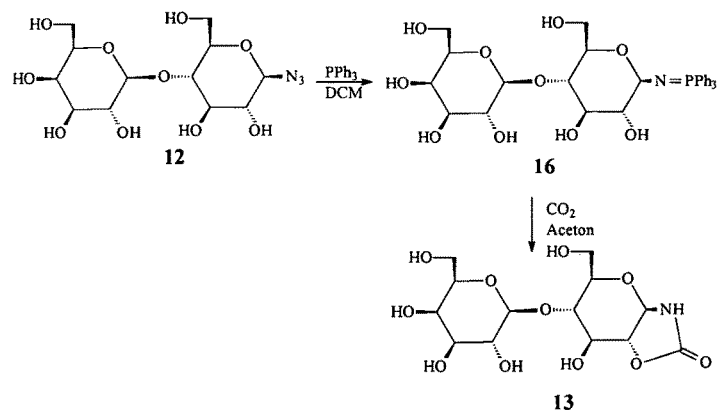
FIG. 6. Preparation of a carbohydrate N,O-cyclic carbamate via phosphinimine intermediate.

Lactosyl-azide 12 (1.8 g) was dissolved in dry DCM (15 mL), and then triphenyl phosphin (1.1 eq.) was added to the mixture was stirred for 3 h (see FIG. 6). Diethyl-ether (50 mL) was added and the white precipitate that formed filtered and washed with cold diethyl-ether affording the phosphinimine 16 (1.9 g).

$CO_2$ was bubbled through the solution of the phosphinimine derivative (1.9 g) in dry acetone (40 mL) at r.t, for 6 h. Then the formed white precipitate collected affording the desired product 13.

Example 18

Figure 7:
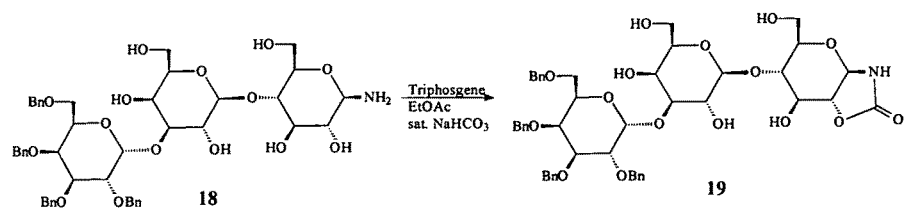
FIG. 7. Preparation of a carbohydrate N,O-cyclic carbamate of an immunogenic carbohydrate.

Triphosgene (1.1 eq.) was added to the solution of α-gal trisaccharide epitope 18 (1 g), in EtOAc and sat $NaHCO_3$, at 0° C. and the mixture was stirred vigorously for 30 min (see FIG. 7). Then the phases are separated, and the organic phase collected, and concentrated. Column chromatography of the residue afforded the product 19.

Example 19

Figure 8:
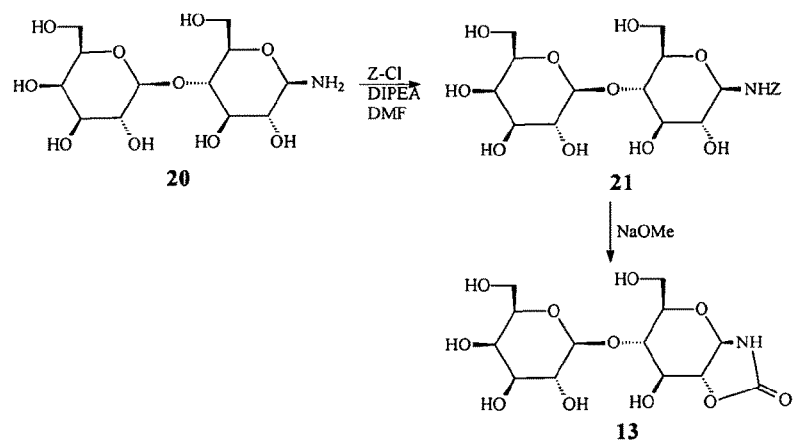
FIG. 8. Preparation of a carbohydrate N,O-cyclic carbamate via intramolecular ring formation of an acyclic carbamate.

Z—Cl (1.2 eq.) was added to the solution of lactosyl-amine 20 (1 g), in DMF in the presence of DIPEA (1.3 eq.) and the mixture was stirred until TLC showed the complete conversion into compound 21 (see FIG. 8). Then NaOMe (1.3 eq.) was added and the mixture was stirred at room temperature. The reaction mixture was neutralized with Amberlite IR 120 ($H^+$) and concentrated. Column chromatography of the residue afforded the product 13.

Example 20

Figure 9:
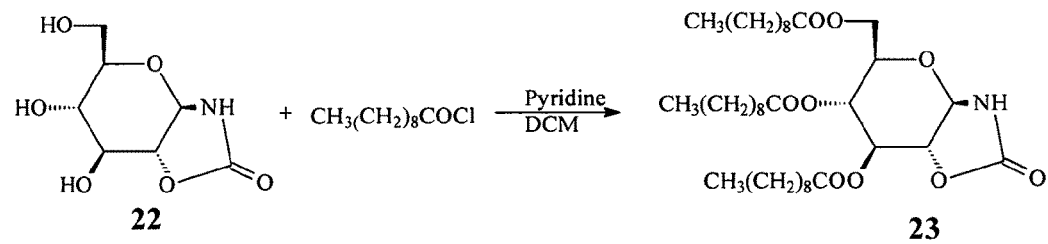
FIG. 9. Preparation of a derivatised carbohydrate N,O-cyclic carbamate.

Acyl chloride (4 eq.) was added to a solution of glucosyl carbamate 22 (100 mg) in DCM (3 mL) and pyridine (4 mL) then the mixture was stirred for overnight, then concentrated and the residue chromatographed affording the product 23 (see FIG. 9).

Example 21

Figure 10:
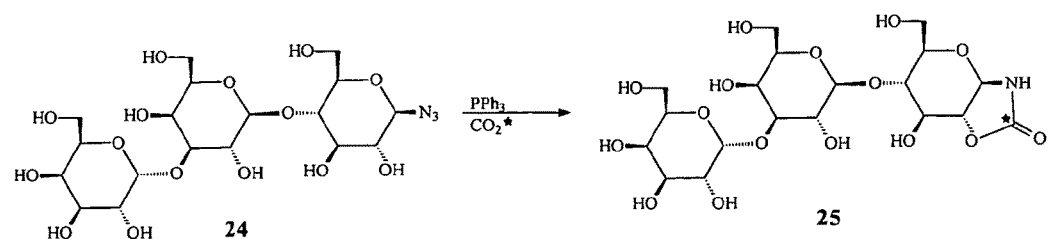
FIG. 10. Preparation of a radioactive labeled trisaccharide with N,O-cyclic carbamate.

$PPh_3$ (31.4 mg) in abs. DMF (0.2 mL) was added to a solution of trisaccharide-azid 24 (50 mg) in abs. DMF (0.3 mL). The mixture stirred for 2 h under inert atmosphere (see FIG. 10). Then 5 mL cc $H_2SO_4$ added to $BaCO_3$ (labeled with C13) (39.4 mg) and the evolved $CO_2$ transferred to the carbohydrate mixture. And the mixture stirred at rt for 8 h. Then the mixture concentrated and triturated with DCM (50 mL) and the product 25 isolated as white solid.

The invention claimed is:

1. A method for the preparation of a carbohydrate-peptide conjugate, said method comprising:
reacting a cyclic carbamate (1) with a peptide,

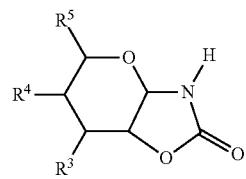

wherein $R^3$ and $R^4$ are independently selected from the group consisting of hydroxyl, acetamido, and a carbohydrate moiety,
$R^5$ is selected from the group consisting of hydrogen, methyl, hydroxymethyl, acetamidomethyl, carboxyl, and X—$(CH_2)_r$—, wherein X is a carbohydrate moiety and r is an integer selected from 0, 1, 2 and 3, and
said peptide includes at least one primary amino group, and said peptide is a cell surface or cell membrane bound protein,
and said carbohydrate-peptide conjugate includes at least one moiety selected from the group consisting of General Formulae 1 and 2

General Formula 1

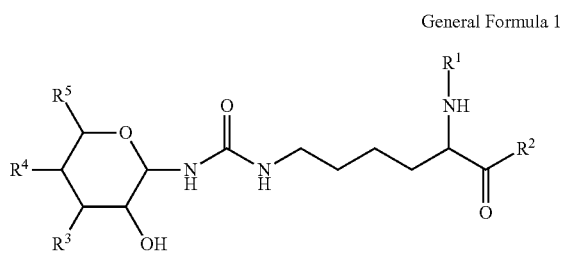

wherein, in General Formula 1,
$R^1$ and $R^2$ together with the intervening lysine moiety represent a cell surface or cell membrane bound protein;
$R^3$, $R^4$ and $R^5$ are as defined at cyclic carbamate (1), and pharmaceutically acceptable salts thereof,
and General Formula 2

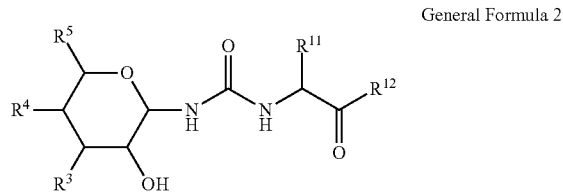

wherein, in General Formula 2,
$R^{11}$ is an amino acid side chain;
$R^{12}$ together with —NH—$CHR^{11}$—C(=O)— represents a cell surface or cell membrane bound protein,
$R^3$, $R^4$ and $R^5$ are as defined at cyclic carbamate (1), and pharmaceutically acceptable salts thereof.

2. The method according to claim 1, wherein the reaction takes place in a polar solvent.

3. The method according to claim 1, wherein the reaction takes place at a pH of in the range of 6.5-10.5.

4. The method according to claim 1, wherein the carbohydrate-peptide conjugate includes at least one moiety selected from the group consisting of General Formulae 1a, 1b and 1c,

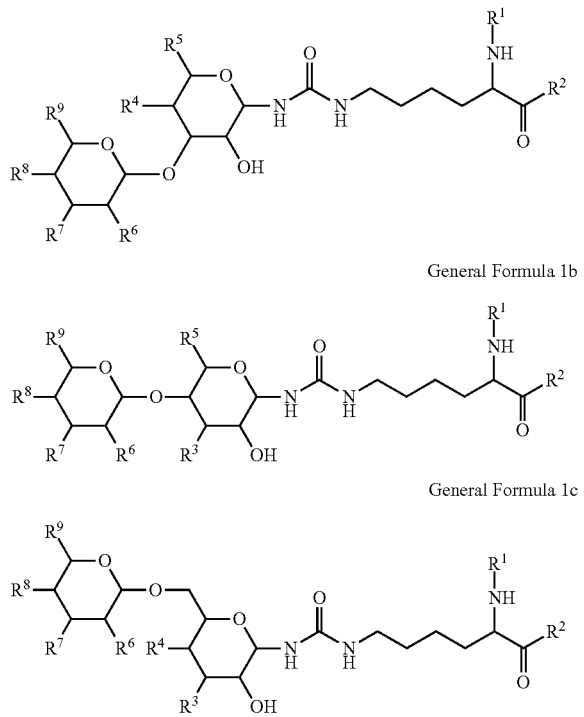

General Formula 1a

General Formula 1b

General Formula 1c wherein,

R¹ and R² together with the intervening lysine moiety represent a cell surface or cell membrane bound protein, $R^6$ and $R^7$ are as defined for $R^3$ and $R^4$ in the General Formula 1, $R^9$ is as defined for $R^5$ in the General Formula 1, and $R^8$ is selected from the group consisting of hydroxyl, $C_{1-6}$-alkoxy, $C_{2-20}$-acyloxy, acetamido, and a carbohydrate moiety.

5. The method according to claim 1, wherein the carbohydrate-peptide conjugate includes at least one moiety selected from the group consisting of General Formulae 2a, 2b and 2c,

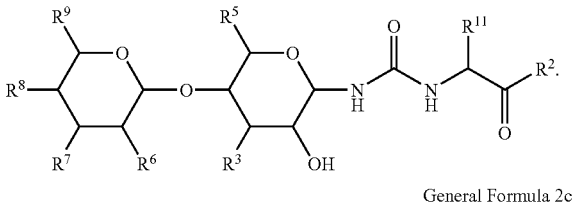

General Formula 2a

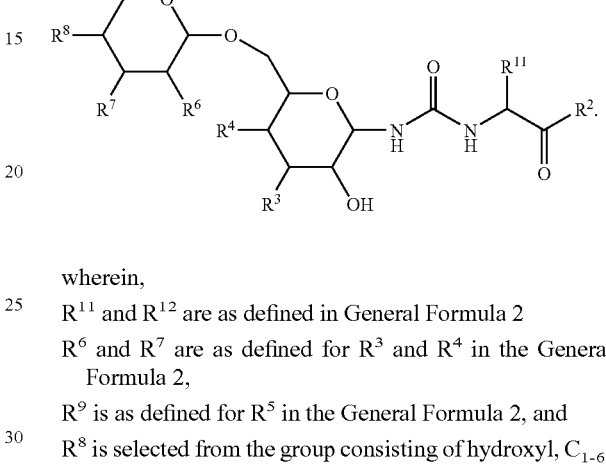

General Formula 2b

General Formula 2c wherein, $R^{11}$ and $R^{12}$ are as defined in General Formula 2

$R^6$ and $R^7$ are as defined for $R^3$ and $R^4$ in the General Formula 2, $R^9$ is as defined for $R^5$ in the General Formula 2, and $R^8$ is selected from the group consisting of hydroxyl, $C_{1-6}$-alkoxy, $C_{2-20}$-acyloxy, acetamido, and a carbohydrate moiety.

6. A carbohydrate-peptide conjugate obtainable by the method according to claim 1.

7. A carbohydrate-peptide conjugate, comprising:

at least one moiety of General Formula 1:

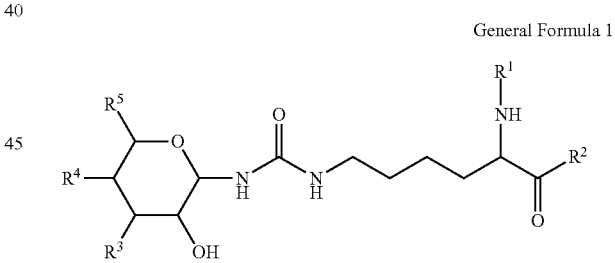

General Formula 1 wherein,

R¹ and R² together with the intervening lysine moiety represent a cell surface or cell membrane bound protein;

$R^3$ and $R^4$ are independently selected from the group consisting of hydroxyl, acetamido, and a carbohydrate moiety, $R^5$ is selected from the group consisting of hydrogen, methyl, hydroxymethyl, acetamidomethyl, carboxyl, and X—(CH2)r-, wherein X is a carbohydrate moiety and r is an integer selected from 0, 1, 2 and 3 and pharmaceutically acceptable salts thereof.

8. The carbohydrate-peptide conjugate according to claim 7, further comprising at least one moiety of any of General Formulae 1a, 1b and 1c,

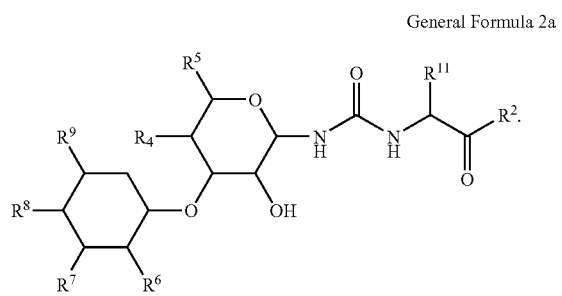

General Formula 1a

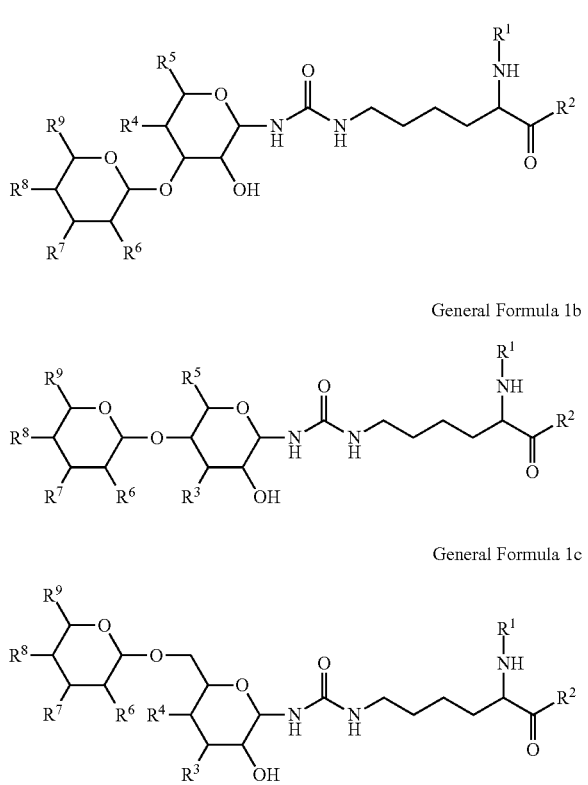

General Formula 1b

General Formula 1c wherein, $R^6$ and $R^7$ are as defined for $R^3$ and $R^4$ in claim 7, $R^9$ is as defined for $R^5$ in claim 7, $R^8$ is selected from the group consisting of hydroxyl, $C_{1-6}$-alkoxy, $C_{2-20}$-acyloxy, acetamido, and a carbohydrate moiety.

9. A carbohydrate-peptide conjugate, comprising:

at least one moiety of the General Formula 2:

General Formula 2

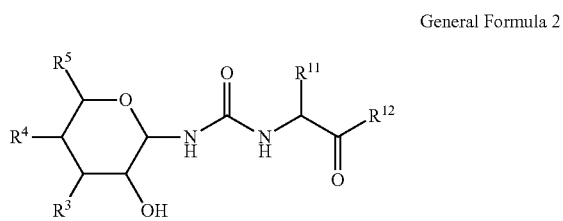

wherein $R^{11}$ is an amino acid side chain;

$R^{12}$ together with —NH—CHR$^{11}$—C(=O)— represents a cell surface or cell membrane bound protein, $R^3$ and $R^4$ are independently selected from the group consisting of hydroxyl, acetamido, and a carbohydrate moiety, $R^5$ is selected from the group consisting of hydrogen, methyl, hydroxymethyl, acetamidomethyl, carboxyl, and X—(CH$_2$)r-, wherein X is a carbohydrate moiety and r is an integer selected from 0, 1, 2 and 3, and pharmaceutically acceptable salts thereof.

10. The carbohydrate-peptide conjugate according to claim 9, further comprising at least one moiety of any of the General Formulae 2a, 2b and 2c, General Formula 2a

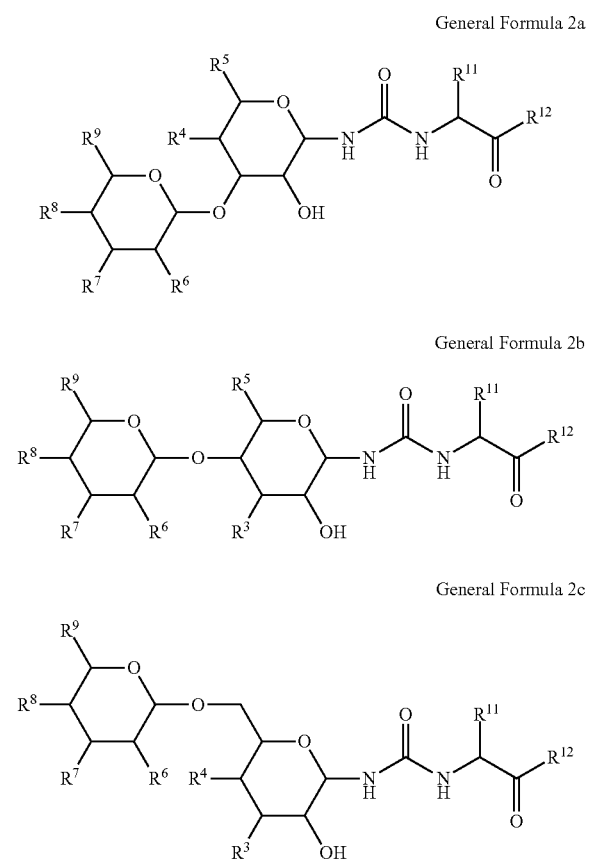

General Formula 2b

General Formula 2c wherein, $R^{11}$ and $R^{12}$ are as defined in claim 9, $R^6$ and $R^7$ are as defined for $R^3$ and $R^4$ in claim 9, $R^9$ is as defined for $R^5$ in claim 9, and $R^8$ is selected from the group consisting of hydroxyl, $C_{1-6}$-alkoxy, $C_{2-20}$-acyloxy, acetamido, and a carbohydrate moiety.

11. The carbohydrate-peptide conjugate according to claim 6, wherein a carbohydrate moiety represents a non-immunogenic carbohydrate.

12. The carbohydrate-peptide conjugate according to claim 6, wherein a carbohydrate moiety represents an immunogenic carbohydrate.

13. The carbohydrate-peptide conjugate according to claim 6, wherein the peptide is a cell-surface or cell-membrane bound protein.

14. The carbohydrate-peptide conjugate as defined in claim 6, the peptide moiety has a total number of amino acid units of at least 30.

15. A pharmaceutical agent, a diagnostic agent, or a diagnostic kit comprising a carbohydrate-peptide conjugate according to claim 6.

16. A cyclic carbamate of an oligosaccharide selected from (4a), (4b) and (4c)

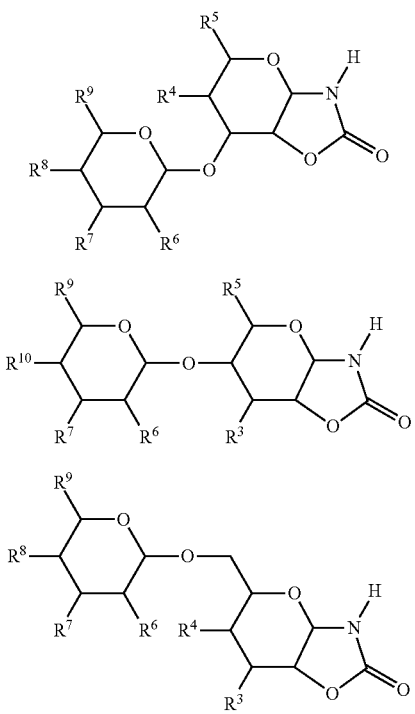

wherein the cyclic carbamate excludes (4-O-β-D-glucopyranosyl-1,2-dideoxy-β-D-glucopyranoso)[1,2-d]oxazolidine-2-one and (4-O-β-D-galactopyranosyl-1,2-dideoxy-β-D-glucopyranoso)[1,2-d]oxazolidine-2-one; and $R^3$, $R^4$, $R^6$ and $R^7$ are independently selected from the group consisting of hydroxyl, acetamido, and a carbohydrate moiety;

$R^5$ and $R^9$ are independently selected from the group consisting of hydrogen, methyl, hydroxymethyl, acetamidomethyl, carboxyl, and X—$(CH_2)r$-, wherein X is a carbohydrate moiety and r is an integer selected from 0, 1, 2 and 3; and $R^8$ and $R^{10}$ are independently selected from the group consisting of hydroxyl, $C_{1-6}$-alkoxy, $C_{1-6}$-acyloxy, acetamido, and a carbohydrate moiety; and pharmaceutically acceptable salts thereof.

17. A carbohydrate-peptide conjugate selected from the group consisting of General Formulae 1 and 2:

General Formula 1

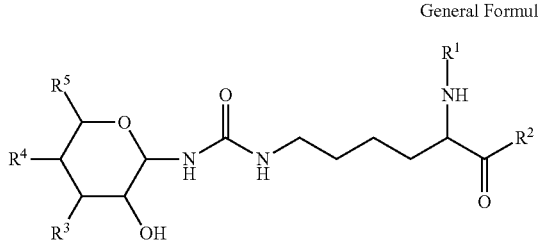

wherein, in General Formula 1,
$R^1$ and $R^2$ together with the intervening lysine moiety represent a cell surface or cell membrane bound protein;
$R^3$ and $R^4$ are independently selected from the group consisting of hydroxyl, acetamido, and a carbohydrate moiety,
$R^5$ is selected from the group consisting of hydrogen, methyl, hydroxymethyl, acetamidomethyl, carboxyl, and X—$(CH_2)_r$—, wherein X is a carbohydrate moiety and r is an integer selected from 0, 1, 2 and 3, and pharmaceutically acceptable salts thereof, and General Formula 2:

General Formula 2

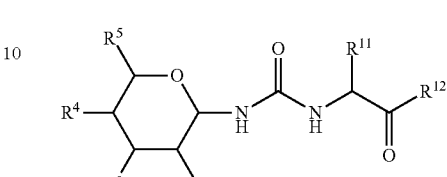

wherein, in General Formula 2,
$R^{11}$ is an amino acid side chain;
$R^{12}$ together with —NH—$CHR^{11}$—C(=O)— represents a cell surface or cell membrane bound protein,
$R^3$ and $R^4$ are independently selected from the group consisting of hydroxyl, acetamido, and a carbohydrate moiety,
$R^5$ is selected from the group consisting of hydrogen, methyl, hydroxymethyl, acetamidomethyl, carboxyl, and X—$(CH_2)_r$—, wherein X is a carbohydrate moiety and
r is an integer selected from 0, 1, 2 and 3, and pharmaceutically acceptable salts thereof.

18. The carbohydrate-peptide conjugate according to claim 17, further comprising at least one moiety of any of the General Formulae 1a, 1b and 1c, General Formula 1a

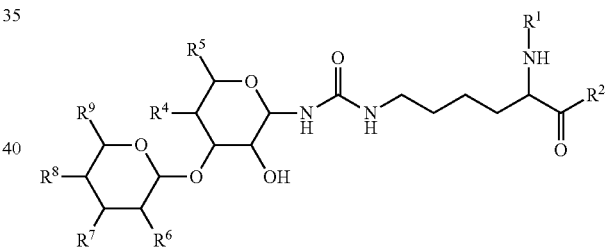

General Formula 1b

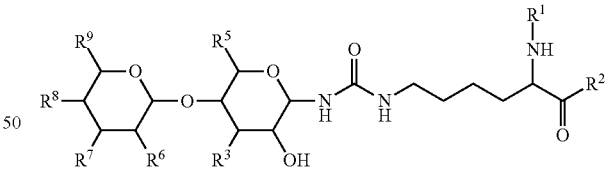

General Formula 1c

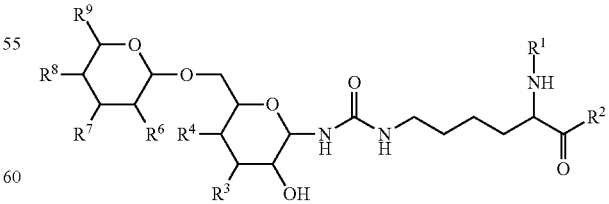

wherein,
$R^1$ and $R^2$ are as defined in claim 17,
$R^6$ and $R^7$ are as defined for $R^3$ and $R^4$ in claim 17,
$R^9$ is as defined for $R^5$ in claim 17, $R^8$ is selected from the group consisting of hydroxyl, $C_{1-6}$-alkoxy, $C_{2-20}$-acyloxy, acetamido, and a carbohydrate moiety.

19. The carbohydrate-peptide conjugate according to claim 17, further comprising at least one moiety of any of the General Formulae 2a, 2b and 2c,

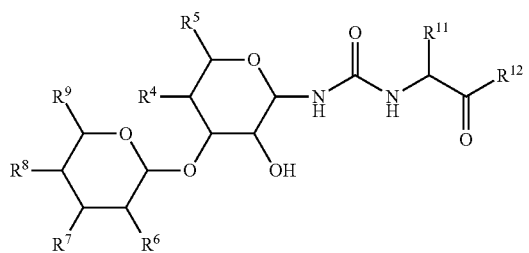

General Formula 2a

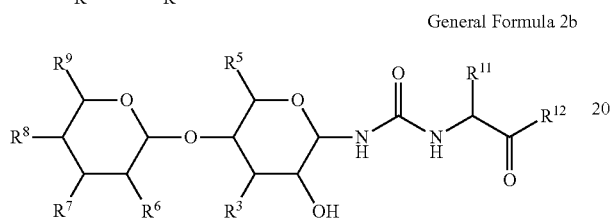

General Formula 2b

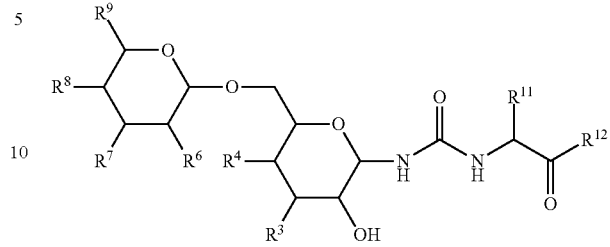

General Formula 2c wherein, $R^{11}$ and $R^{12}$ are as defined in claim 17, $R^6$ and $R^7$ are as defined for $R^3$ and $R^4$ in claim 17, $R^9$ is as defined for $R^5$ in claim 17, and $R^8$ is selected from the group consisting of hydroxyl, $C_{1-6}$-alkoxy, $C_{2-20}$-acyloxy, acetamido, and a carbohydrate moiety.

* * * * *